US009305218B2

(12) United States Patent
Lewis et al.

(10) Patent No.: US 9,305,218 B2
(45) Date of Patent: Apr. 5, 2016

(54) METHODS AND SYSTEMS FOR IDENTIFYING, MARKING, AND INVENTORYING LARGE QUANTITIES OF UNIQUE SURGICAL INSTRUMENTS

(71) Applicant: Prezio Health, Troy, MI (US)

(72) Inventors: Russell F. Lewis, Dallas, TX (US); Dennis Streppa, Lake Bluff, IL (US); Gary Keith Stroud, Kaysville, UT (US)

(73) Assignee: PREZIO HEALTH, Troy, MI (US)

( * ) Notice: Subject to any disclaimer, the term of this patent is extended or adjusted under 35 U.S.C. 154(b) by 124 days.

(21) Appl. No.: 13/830,688

(22) Filed: Mar. 14, 2013

(65) Prior Publication Data

US 2013/0336554 A1 Dec. 19, 2013

Related U.S. Application Data

(60) Provisional application No. 61/659,861, filed on Jun. 14, 2012.

(51) Int. Cl.
*G06K 9/00* (2006.01)
*G06F 17/30* (2006.01)
*G06F 19/00* (2011.01)

(52) U.S. Cl.
CPC ...... *G06K 9/00771* (2013.01); *G06F 17/30943* (2013.01); *G06F 19/324* (2013.01); *G06F 19/327* (2013.01); *G06K 9/00* (2013.01); *G06K 2209/05* (2013.01)

(58) Field of Classification Search
None
See application file for complete search history.

(56) References Cited

U.S. PATENT DOCUMENTS

| | | |
|---|---|---|
| 6,882,409 B1 | 4/2005 | Evans et al. |
| 7,093,755 B2 | 8/2006 | Jordan et al. |
| 7,268,684 B2 | 9/2007 | Tethrake et al. |
| 7,362,228 B2 | 4/2008 | Nycz et al. |
| 7,492,257 B2 | 2/2009 | Tethrake et al. |
| 7,837,694 B2 | 11/2010 | Tethrake et al. |
| 8,006,903 B2 | 8/2011 | Braun et al. |
| 8,020,768 B2 | 9/2011 | Ramos-Elizondo et al. |

(Continued)

FOREIGN PATENT DOCUMENTS

WO WO-2009/003231 1/2009

OTHER PUBLICATIONS

Vinutha Kallem and Noah Cowan. "Image-guided control of Flexible Bevel-Tip Needles" NIH Publication, IEEE Int Conf Robot Autom. Apr. 10, 2007; 2007: 3015-3020. doi:10.1109/ROBOT.2007.363930, Feb. 23, 2011, Kallem teaches.*

*Primary Examiner* — Bhavesh Mehta
*Assistant Examiner* — Oneal R Mistry
(74) *Attorney, Agent, or Firm* — Morrison & Foerster LLP

(57) ABSTRACT

An apparatus for automatically identifying a surgical instrument, the apparatus comprising a capture module, an attribute database, a comparison module, and an exporting module, the capture module comprising hardware operable to capture multiple attributes of the surgical instrument, the attribute database comprising multiple stored attributes of a plurality of reference surgical instruments, the comparison module programmed to generate a comparison score for the surgical instrument, wherein the comparison module is programmed to generate the comparison score by receiving multiple attributes captured by the capture module and comparing it to the multiple attributes stored in the attribute database, and the exporting module configured to receive and export the comparison score generated by the comparison module.

13 Claims, 11 Drawing Sheets

(56) References Cited

U.S. PATENT DOCUMENTS

| | | |
|---|---|---|
| 8,177,776 B2 | 5/2012 | Humayun et al. |
| 2008/0004603 A1* | 1/2008 | Larkin .................. A61B 19/52 606/1 |
| 2011/0005342 A1* | 1/2011 | Treat et al. ................... 73/865.8 |
| 2011/0114522 A1 | 5/2011 | Alston et al. |
| 2011/0245963 A1 | 10/2011 | Leng |
| 2012/0169470 A1 | 7/2012 | Lee |
| 2014/0328517 A1* | 11/2014 | Gluncic ........................ 382/103 |
| 2014/0341424 A1* | 11/2014 | Reiter et al. .................. 382/103 |

* cited by examiner

300 → 302 304 306

| Reference Instrument | Attribute 1 (Size) | Attribute 2 (Weight) |
|---|---|---|
| Instrument 1 | 2" x 4" | 1.0 lbs |
| Instrument 2 | 2" x 3" | 1.1 lbs |
| Instrument 3 | 1" x 1" | 0.8 lbs |
| Instrument 4 | 2" x 3" | 1.1 lbs |
| Instrument 5 | 4" x 3" | 2.0 lbs |
| ⋮ | ⋮ | ⋮ |
| Instrument i | 1" x 2" | 0.9 lbs |

| Attribute 1 (Weight) | Reference Instruments |
|---|---|
| 0.8 lbs | Instrument 3 |
| 0.9 lbs | Instrument i |
| 1.0 lbs | Instrument 1 |
| 1.1 lbs | Instrument 2 |
|  | Instrument 4 |
| ⋮ | ⋮ |
| 2.0 lbs | Instrument 5 |

FIGURE 3B

METHODS AND SYSTEMS FOR IDENTIFYING, MARKING, AND INVENTORYING LARGE QUANTITIES OF UNIQUE SURGICAL INSTRUMENTS

CROSS-REFERENCE TO RELATED APPLICATIONS

This application claims the benefit of U.S. Provisional Application No. 61/659,861, filed Jun. 14, 2012, the disclosure of which is incorporated by reference herein in its entirety.

FIELD OF THE INVENTION

This invention relates generally to surgical instruments, and more particularly, to methods and systems for automatically identifying, marking, and inventorying surgical instruments.

BACKGROUND OF THE INVENTION

Many Health Care Organizations (HCOs) have large investments (millions of dollars) in surgical instruments, but lack the ability to effectively manage their surgical instrument inventory. In most HCOs, there are hundreds, if not thousands, of unique instrument types, and tens of thousands (in some cases hundreds of thousands) of individual instruments.

The ability to accurately identify unique surgical instruments from a large quantity of instruments is essential to many of the basic processes in the perioperative environment. The need to identify surgical instruments is shared by many individuals serving in many different roles within the HCO. There is a steep learning curve to obtain familiarity with even the most common instruments types, which leads to frequent misidentification of instruments. The sheer number of instruments makes manual instrument identification impractical.

A significant number of surgical instruments are lost, stolen, or broken in HCOs on an annual basis and most HCOs do not even attempt to maintain an accurate inventory of surgical instruments because of the challenges and labor costs associated in instrument identification. When HCO's inventory their surgical instruments, the inventory process is typically performed manually, leading to many of the problems discussed above.

SUMMARY OF THE INVENTION

The presently disclosed embodiments are directed to solving one or more of the problems presented in the prior art, described above, as well as providing additional features that will become readily apparent by reference to the following detailed description when taken in conjunction with the accompanying drawings.

In a first embodiment, an apparatus automatically identifies a surgical instrument and the apparatus comprises a capture module, an attribute database, a comparison module, and an exporting module. The capture module comprises hardware operable to capture multiple attributes of the surgical instrument. The attribute database comprising multiple stored attributes of a plurality of reference surgical instruments. The comparison module is programmed to generate a comparison score for the surgical instrument, wherein the comparison module is programmed to generate the comparison score by receiving multiple attributes captured by the capture module and comparing it to the multiple attributes stored in the attribute database. The exporting module is configured to receive and export the comparison score generated by the comparison module.

A second embodiment according to the first embodiment, wherein the capture module comprises one or more devices selected from the group consisting of an image capture device, a weight capture device, a color capture device, a material-type capture device, and a surface-type capture device.

A third embodiment according to the second embodiment, wherein the capture module comprises the image capture device, and wherein the image capture device comprises at least a first camera configured to capture a first image of the surgical instrument.

A fourth embodiment according to the third embodiment, wherein the comparison module is programmed to generate the comparison score by at least comparing the first image of the surgical instrument to stored images of the plurality of reference surgical instruments.

A fifth embodiment according to the third or fourth embodiments, wherein the image capture device further comprises at least a second camera configured to capture a second image of the surgical instrument, wherein the first and second cameras are relatively positioned to capture respective first and second perspectives of the surgical instrument, and wherein the comparison module is programmed to generate the comparison score by at least comparing the first and second images of the surgical instrument to the stored images of the plurality of reference surgical instruments.

A sixth embodiment according to any of the third through fifth embodiments, wherein the image capture device further comprises a reference grid for obtaining dimensions of the surgical instrument, wherein the attribute database comprises stored dimensions of the plurality of reference surgical instruments, and wherein the comparison module is programmed to generate the comparison score by at least comparing the dimensions of the surgical instrument to stored dimensions of the plurality of reference surgical instruments.

A seventh embodiment according to any of the third through sixth embodiments, wherein the image capture device is configured to capture an image of teeth of the surgical instrument, and wherein the comparison module is programmed to generate the comparison score by at least comparing the captured image of the teeth of the surgical instrument to stored images of teeth of the plurality of reference surgical instruments.

An eighth embodiment according to the any of the first through seventh embodiments, wherein the comparison module generates the comparison score by generating a first sub-set of the plurality of reference surgical instruments, wherein the first sub-set comprises one or more of the plurality of reference surgical instruments that exceed a threshold comparison value for one of the at least one stored attribute of the plurality of reference surgical instruments.

A ninth embodiment according to the eight embodiment, wherein the comparison module is programmed to generate the comparison score by comparing a third of the multiple attributes of the surgical instrument to a third of the multiple attributes of the plurality of reference surgical instruments.

A tenth embodiment according to any of the first through ninth embodiments, wherein the exporting module comprises a display for displaying the comparison score.

In an eleventh embodiment, an apparatus for marking a surgical instrument comprises a mark-identification module, an instrument identification module, and an instrument marking module. The mark-identification module is operable to determine whether the surgical instrument comprises an identification mark. The instrument identification module is operable to generate an identity of the surgical instrument when the mark-identification module determines that the surgical instrument does not comprise an identification mark. The instrument marking module is operable to generate an identification mark for the surgical instrument based on the identity of the surgical instrument generated by the instrument identification module.

A twelfth embodiment according to the eleventh embodiment, wherein the instrument identification module further comprises a capture module comprising hardware operable to capture multiple attributes of the surgical instrument, an attribute database comprising multiple stored attributes of a plurality of reference surgical instruments, a comparison module programmed to generate a comparison score for the surgical instrument, wherein the comparison module is programmed to generate the comparison score by receiving the multiple attributes captured by the capture module and comparing it to the multiple attributes stored in the attribute database, and an exporting module configured to receive and export the comparison score generated by the comparison module.

In a thirteenth embodiment, a method of identifying a surgical instrument comprises capturing multiple attributes of the surgical instrument, comparing the multiple attributes to multiple attributes of a plurality of reference instruments, wherein the multiple attributes of the plurality of reference instruments is stored in an attribute database, generating a comparison score for the surgical instrument, wherein the comparison score is based on the comparing the multiple captured attributes to the multiple stored attributes of a plurality of reference instruments, and exporting the comparison score.

A fourteenth embodiment according to the thirteenth embodiment, wherein capturing the multiple attributes comprises capturing one or more attributes selected from the group consisting of an image of the surgical instrument, a dimension of the surgical instrument, a weight of the surgical instrument, a color of the surgical instrument, a material-type of the surgical instrument, and a surface-type of the surgical instrument.

A fifteenth embodiment according to the fourteenth embodiment, wherein capturing the multiple attributes comprises capturing at least a dimension of the surgical instrument, and wherein comparing the multiple captured attributes comprises comparing at least the dimension of the surgical instrument to stored dimensions of the plurality of reference surgical instruments.

A sixteenth embodiment according to any of the thirteenth through fifteenth embodiments, wherein capturing the multiple attributes comprises capturing at least a first image of the surgical instrument.

A seventeenth embodiment according to any of the thirteenth through sixteenth embodiments, wherein comparing the multiple captured attributes comprises at least comparing the first image of the surgical instrument to stored images of the plurality of reference surgical instruments.

An eighteenth embodiment according to any of the thirteenth through seventeenth embodiments, wherein capturing the multiple attributes comprises capturing at least a second image of the surgical instrument, wherein the first and second images provide respective first and second perspectives of the surgical instrument, and wherein comparing the multiple captured attributes comprises at least comparing the first and second images of the surgical instrument to stored images of the plurality of reference surgical instruments.

A nineteenth embodiment according to any of the thirteenth through eighteenth embodiments, wherein capturing the multiple attributes comprises capturing an image of teeth of the surgical instrument, and wherein comparing the multiple captured attributes comprises at least comparing the image of the teeth of the surgical instrument to stored images of teeth of the plurality of reference surgical instruments.

A twentieth embodiment according to any of the thirteenth through ninteenth embodiments, wherein generating the comparison score comprises generating a first sub-set of the plurality of reference surgical instruments, wherein the first sub-set comprises one or more of the plurality of reference surgical instruments that exceed a threshold comparison value for one of the at least one stored attribute of the plurality of reference surgical instruments.

A twenty-first embodiment according to any of the thirteenth through twentieth embodiments, wherein generating the comparison score comprises comparing a second of the at least one captured attribute of the surgical instrument to a second of the at least one stored attribute of the plurality of reference surgical instruments.

A twenty-second embodiment according to any of the thirteenth through twenty-first embodiments, wherein exporting the comparison score comprises displaying the comparison score.

In a twenty-third embodiment, a method for marking a surgical instrument comprises determining whether the surgical instrument comprises an identification mark, generating an identity of the surgical instrument when the surgical instrument is determined not to comprise an identification mark, and generating an identification mark for the surgical instrument based on the generated identity of the surgical instrument.

A twenty-fourth embodiment according to the twenty-third embodiment, wherein generating an identity of the surgical instrument comprises capturing multiple attributes of the surgical instrument, comparing the multiple captured attributes to multiple attributes of a plurality of reference instruments, wherein the multiple attributes of the plurality of reference instruments are stored in an attribute database, generating a comparison score for the surgical instrument, wherein the comparison score is based on the comparing multiple captured attributes to multiple attributes of a plurality of reference instruments, and exporting the comparison score.

In a twenty-fifth embodiment, a method of building a database of at least one attribute of each of a plurality of reference materials, the method comprising determining whether a surgical instrument comprises an identification mark, capturing the at least one attribute of the surgical instrument when the surgical instrument is determined not to comprise an identification mark, generating an identity of the surgical instrument, and exporting the at least one attribute and the identity of the surgical instrument to the database.

A twenty-sixth embodiment according to the twenty-fifth embodiment, further comprising accessing a manufacturer's database to obtain the at least one attribute.

A twenty-seventh embodiment according to the twenty-fifth or twenty-sixth embodiments, wherein generating an identity of the surgical instrument comprises capturing multiple attributes of the surgical instrument, comparing the multiple attributes to multiple attributes of a plurality of reference instruments, wherein the multiple attributes of the plurality of reference instruments are stored in an attribute database, generating a comparison score for the surgical instrument, wherein the comparison score is based on the comparing the multiple captured attribute to multiple attributes of a plurality of reference instruments, and exporting the comparison score.

In a twenty-eight embodiment, a computer readable medium containing executable instructions that when executed perform a method of identifying a surgical instrument, the method comprising capturing multiple attributes of the surgical instrument, comparing the multiple attributes to multiple attributes of a plurality of reference instruments (wherein the multiple attributes of the plurality of reference instruments is stored in an attribute database), generating a comparison score for the surgical instrument (wherein the comparison score is based on the comparing the at least one captured attribute to the at least one stored attribute of a plurality of reference instruments), and exporting the comparison score.

A twenty-ninth embodiment according to the twenty-eight embodiment, wherein capturing the multiple attributes comprises capturing one or more attributes selected from the group consisting of an image of the surgical instrument, a dimension of the surgical instrument, a weight of the surgical instrument, a color of the surgical instrument, a material-type of the surgical instrument, and a surface-type of the surgical instrument.

A thirtieth embodiment according to the twenty-seventh or twenty-ninth embodiments, wherein capturing the multiple attributes comprises capturing at least a dimension of the surgical instrument, and wherein comparing the at least one captured attribute comprises comparing at least the dimension of the surgical instrument to stored dimensions of the plurality of reference surgical instruments.

A thirty-first embodiment according to any of the twenty-eight through thirtieth embodiments, wherein capturing the multiple attributes comprises capturing at least a first image of the surgical instrument.

A thirty-second embodiment according to any of the twenty-eight through thirty-first embodiments, wherein comparing the at least one captured attribute comprises at least comparing the first image of the surgical instrument to stored images of the plurality of reference surgical instruments.

A thirty-third embodiment according to any of the twenty-eight through thirty-second embodiments, wherein capturing the multiple attributes comprises capturing at least a second image of the surgical instrument, wherein the first and second images provide respective first and second perspectives of the surgical instrument, and wherein comparing the at least one captured attribute comprises at least comparing the first and second images of the surgical instrument to stored images of the plurality of reference surgical instruments.

A thirty-fourth embodiment according to any of the twenty-eight through thirty-third embodiments, wherein capturing the multiple attributes comprises capturing an image of teeth of the surgical instrument, and wherein comparing the at least one captured attribute comprises at least comparing the image of the teeth of the surgical instrument to stored images of teeth of the plurality of reference surgical instruments.

A thirty-fifth embodiment according to any of the twenty-eight through thirty-fourth embodiments, wherein generating the comparison score comprises generating a first sub-set of the plurality of reference surgical instruments, wherein the first sub-set comprises one or more of the plurality of reference surgical instruments that exceed a threshold comparison value for one of the at least one stored attribute of the plurality of reference surgical instruments.

A thirty-sixth embodiment according to any of the twenty-eight through thirty-fifth embodiments, wherein generating the comparison score comprises comparing a second of the at least one captured attribute of the surgical instrument to a second of the at least one stored attribute of the plurality of reference surgical instruments.

In a thirty seventh embodiment, a computer readable medium containing executable instructions that when executed perform a method of marking a surgical instrument, the method comprising determining whether the surgical instrument comprises an identification mark, generating an identity of the surgical instrument when the surgical instrument is determined not to comprise an identification mark, and generating an identification mark for the surgical instrument based on the generated identity of the surgical instrument.

A thirty-eight embodiment according to the thirty-seventh embodiment, wherein generating an identity of the surgical instrument comprises capturing multiple attributes of the surgical instrument, comparing the at least one captured attribute to multiple attributes of a plurality of reference instruments, wherein the multiple attributes of the plurality of reference instruments is stored in an attribute database, generating a comparison score for the surgical instrument, wherein the comparison score is based on the comparing at least one captured attribute to multiple attributes of a plurality of reference instruments, and exporting the comparison score.

In a thirty-ninth embodiment, a computer readable medium containing executable instructions that when executed perform a method of building a database of multiple attributes of each of a plurality of reference materials, the method comprising determining whether a surgical instrument comprises an identification mark, capturing the multiple attributes of the surgical instrument when the surgical instrument is determined not to comprise an identification mark, generating an identity of the surgical instrument, and exporting the multiple attributes and the identity of the surgical instrument to the database.

A fortieth embodiment according to the thirty-ninth embodiment, wherein the method further comprises accessing a manufacturer's database to obtain the multiple attributes.

A forty-first embodiment according to the thirty-ninth or fortieth embodiments, wherein generating an identity of the surgical instrument comprises capturing multiple attributes of the surgical instrument, comparing the multiple attributes to multiple attributes of a plurality of reference instruments, wherein the multiple attributes of the plurality of reference instruments are stored in an attribute database, generating a comparison score for the surgical instrument, wherein the comparison score is based on the comparing at least one captured attribute to multiple attributes of a plurality of reference instruments, and exporting the comparison score.

In a forty-second embodiment, a reference database storing attributes of a plurality of reference surgical instruments, the database created by a method comprising determining whether a surgical instrument comprises an identification mark, capturing the multiple attributes of the surgical instrument when the surgical instrument is determined not to comprise an identification mark, generating an identity of the surgical instrument, and exporting the multiple attributes and the identity of the surgical instrument to the database.

A forty-third embodiment according to the forty-second embodiment, wherein the method further comprises accessing a manufacturer's database to obtain the multiple attributes.

A forty-fourth embodiment according to the forty-second or forty-third embodiments, wherein generating an identity of the surgical instrument comprises capturing multiple attributes of the surgical instrument, comparing the multiple attributes to multiple attributes of a plurality of reference instruments, wherein the multiple attributes of the plurality of reference instruments are stored in an attribute database, generating a comparison score for the surgical instrument, wherein the comparison score is based on the comparing at least one captured attribute to multiple attributes of a plurality of reference instruments, and exporting the comparison score.

It is to be understood that both the foregoing general description and the following detailed description are exemplary and are merely intended to provide further explanation of the claimed subject matter.

BRIEF DESCRIPTION OF THE DRAWINGS

The features, nature and advantages of the present disclosure will become more apparent from the detailed description set forth below when taken in conjunction with the drawings in which like reference characters identify correspondingly throughout and wherein:

FIG. 3A illustrates a reference database, in accordance with an embodiment of the invention.

FIG. 3B illustrates a reference database, in accordance with an embodiment of the invention.

DETAILED DESCRIPTION OF EXEMPLARY EMBODIMENTS OF THE INVENTION

Figure 1:
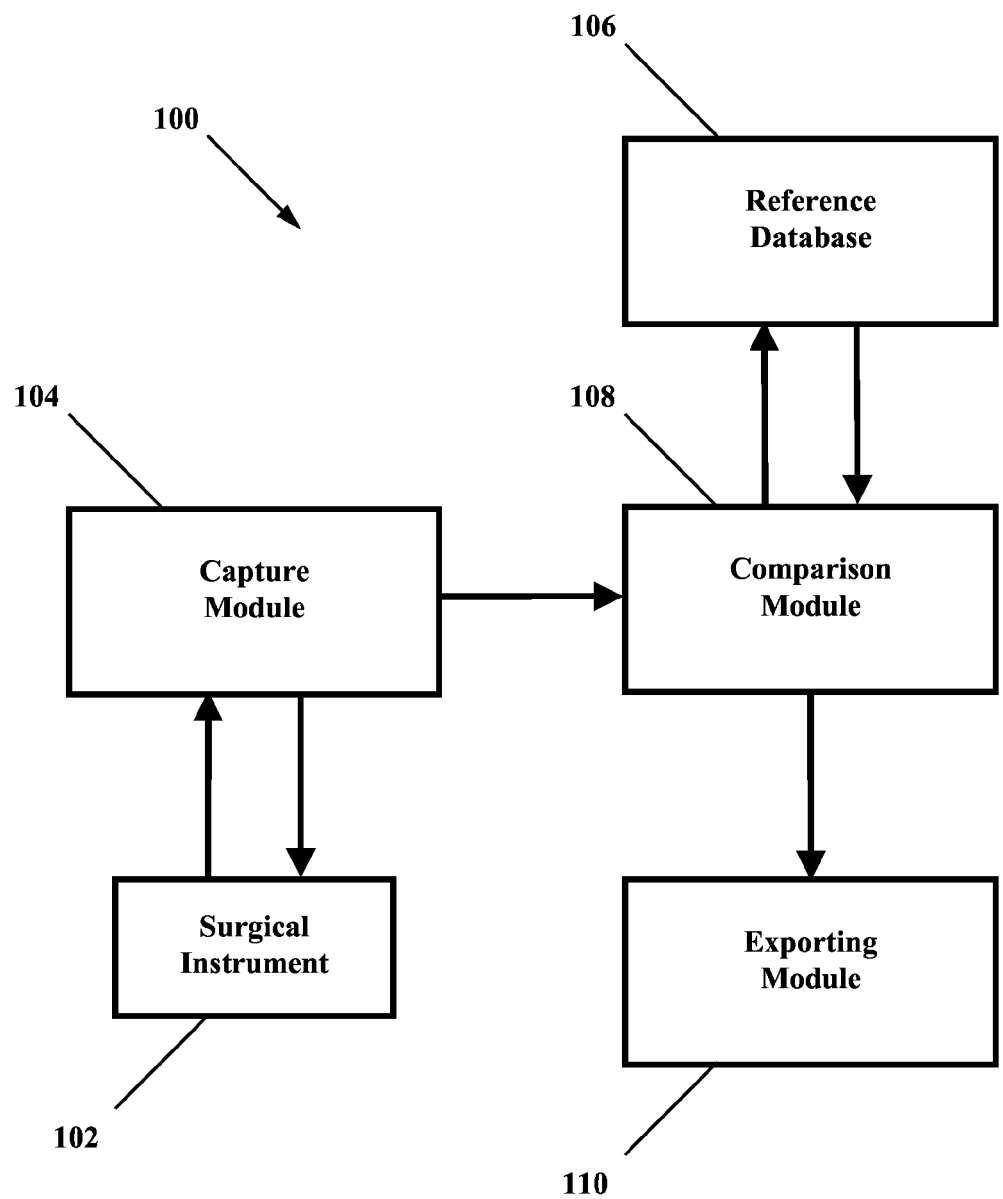
FIG. 1 is a block diagram of an exemplary system for automatic identification of a surgical instrument, in accordance with an embodiment of the invention.

In the following description of exemplary embodiments, reference is made to the accompanying drawings which form a part hereof, and in which it is shown by way of illustration specific embodiments in which the invention may be practiced. It is to be understood that other embodiments may be utilized and structural changes may be made without departing from the scope of the present invention.

The word "exemplary" is used herein to mean "serving as an example or illustration." Any aspect or design described herein as "exemplary" is not necessarily to be construed as preferred or advantageous over other aspects or designs.

It should be understood that the specific order or hierarchy of steps in the processes disclosed herein is an example of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Reference will now be made in detail to aspects of the subject technology, examples of which are illustrated in the accompanying drawings, wherein like reference numerals refer to like elements throughout.

Disclosed herein are methods and systems for the automatic identification, marking, and inventorying of surgical instruments. These methods and systems may enhance the efficiency and accuracy of the instrument-identification process.

FIG. 1 is a block diagram of an exemplary System 100 for automatic identification of a Surgical Instrument 102, in accordance with an embodiment of the invention. Surgical Instrument 102 may be one of a plurality of unique surgical instruments. System 100 includes Capture Module 104, Reference Database 106, Comparison Module 108, and Exporting Module 110. Capture Module 104 captures an attribute of Surgical Instrument 102 and transmits the captured attribute to the Comparison Module 108. Comparison Module 108 accesses the Reference Database 106, wherein attributes are stored for a plurality of reference surgical instruments. The Comparison Module 108 compares the captured attribute to the stored attributes and generates a comparison score for one or more reference surgical instruments. An Exporting Module 110 then exports the comparison score(s) generated by the Comparison Module 108.

Capture Module 104 may be any device capable of obtaining an attribute of the surgical instrument. The attribute may include a shape, a size, a weight, a color, a material-type, or a surface-type of the surgical instrument. In some embodiments, Capture Module 104 may comprise a device capable of obtaining multiple attributes, such as a combination of any of the foregoing attributes. In yet other embodiments, Capture Module 104 may comprise a device capable of obtaining other attributes, in addition to or in lieu of the foregoing attributes, where such attributes aid in distinguishing one surgical instrument from another.

Figure 2:
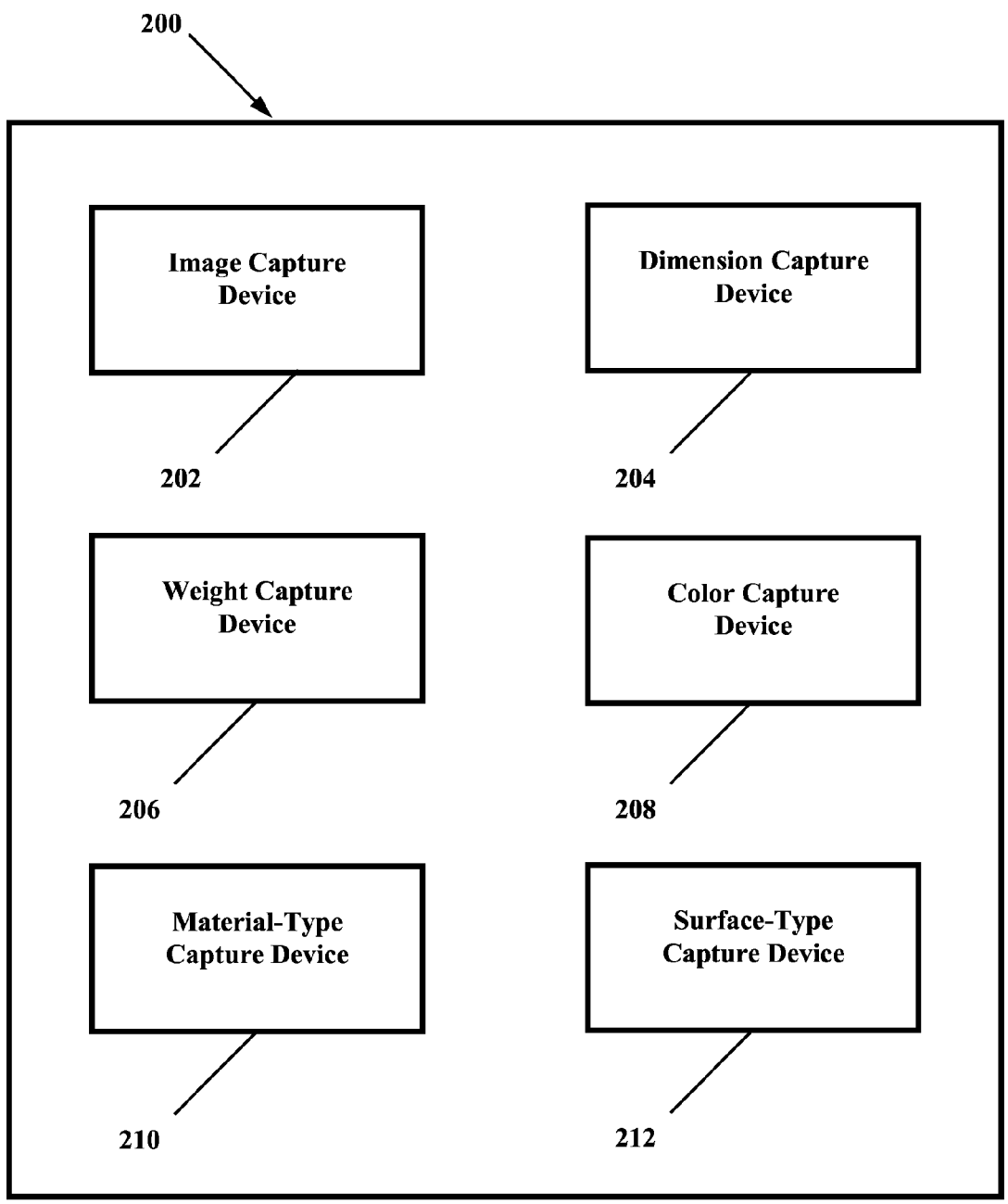
FIG. 2 is a block diagram of a capture module, in accordance with an embodiment of the invention.

FIG. 2 is a block diagram of a Capture Module 200 in accordance with an embodiment of the invention. In some embodiments, Capture Module 200 corresponds to Capture Module 100 described above with respect to FIG. 1. Capture Module 200 includes multiple devices, each operable to capture an individual attribute. Capture Module 200 includes Image Capture Device 202, Dimension Capture Device 204, Weight Capture Device 206, Color Capture Device 208, Material-Type Capture Device 210, and Surface-Type Capture Device 212. Capture Module 200 may utilize any of the devices 202-210 for identifying a surgical instrument.

In some embodiments, Capture Module 200 utilizes devices 202-212 in series until an identity of the surgical instrument is determined. For example, Capture Module 200 may first capture an image of the surgical instrument and, if the image is insufficient to identify the surgical instrument, may then proceed to capturing the weight of the device. If the surgical instrument is not yet identified, Capture Module 200 may continue utilizing additional sub-devices until the instrument is identified. Capture Module 200 may utilize the devices in any order.

The number and variance of devices within Capture Module 200 may allow the module to accurately identify each one of a large number of unique surgical instruments. More specifically, a large percentage of instruments within an instrument type may comprise subtle differences, thereby making accurate identification based on a single attribute challenging. As used herein, an instrument type can be understood to refer to a particular category of instruments (such as scissors, scalpels, etc.) or to a particular sub-category of instruments (such as stainless-steel scalpels, etc.). Using multiple attributes to refine the search may yield more accurate and dependable identifications.

Although Capture Module 200 depicts only one of each device, other embodiments may include more than one of each device. For example, Capture Module 200 may include more than one Image Capture Device, wherein each Image Capture Device captures a different perspective of the surgical instrument.

In some embodiments, an image captured by Image Capture Device 202 may be analyzed by image recognition software to determine a shape of the surgical instrument. In further embodiments, the spacing or shape of the teeth of a surgical instrument may be determined by the image recognition software. In other embodiments, the size and shape of handles of a surgical instrument may be determined by the image recognition software. In yet other embodiments, the position and size of joints of a surgical instrument may be determined by the image recognition software. In some other embodiments, original and distinctive manufacturer markings (such as a manufacturer's logo) may be captured and determined. In further embodiments, a combination of any of the foregoing attributes is determined by the image recognition software.

As used herein, image recognition can be understood to be the identification of physical form of an object. For example, image recognition may comprise determining a two-dimensional outline of an object's shape. Image recognition may comprise determining an object's interior features In other embodiments, Image Capture Device 202 is operable to capture the dimensions of a surgical instrument. In this embodiment, Image Capture Device 202 may include a reference grid from which image recognition software can obtain dimensions. For example, the lines of the reference grid may be spaced 1 cm apart. By determining the number of squares of the grid occupied by the surgical instrument, the image recognition software can determine an approximate size of the instrument in two dimensions. A second camera and a second reference grid may also be used to provide a third dimension. As such, Image Capture Device 202 may comprise Dimension Capture Device 204, explained in more detail below. In some embodiments, providing a range of dimensions may facilitate identification of an instrument in its open or closed positions. In such embodiments, a reference database of surgical instruments may include a range of dimensions corresponding to a plurality of different states. For example, the reference database may include the range of dimensions of a scissors from its open to closed states. In some embodiments, the dimensions of multiple states may be included. In some further embodiments, the states may not correspond to a range between two extremes, such as open and closed, and may correspond to a variety of different and unique states. As an exemplary advantage to this feature, the system is not sensitive to the state of the instrument when it is attempting to identify the instrument. In this way, users may introduce surgical instruments into the system without the need to orient the instrument in a particular, predetermined manner, thereby improving the ease with which the system can be used and reducing the need for user intervention. In other embodiments, the instrument may be entered in a specific state and/or orientation, thereby further limiting the number of possible matches and improving identification accuracy.

In some embodiments, Dimension Capture Device 204 is configured to automatically capture one or more dimensions of the instrument. For example, a laser system may be employed to capture the dimensions (and external outline) of the device. The laser system may include a sensor on the side opposite the source of laser beam, wherein the sensor identifies when a laser beam is interrupted. More specifically, a laser may be linearly swept across the device and the point at which the beam is first broken (corresponding to an outer dimension of the surgical instrument) is determined. In other embodiments, other light waves may be directed to the instrument and either a sensor on the opposite side of the device detects when the beam is first interrupted or reflections from the instrument are analyzed. Apparatuses to transmit and analyze reflected light waves include Laser Detection and Ranging ("LADAR") devices, such as those disclosed in U.S. Pat. No. 6,882,409, titled "Multi-spectral LADAR," the entirety of which is incorporated herein by reference for all purposes. In this embodiment, a two dimensional grid may be divided into pixels—that is, sub-regions—and the distance to the object determined. In this way, a LADAR system could be used to determine the topography of one or more faces of the device, in addition to the dimension attributes of the device. In other embodiments, the dimension attributes of a surgical instrument may be captured using movable walls to size each dimension. For example, a surgical instrument may be placed between two walls which are configured to move toward one another and touch the instrument. Once both walls are determined to be touching the instrument, the distance between the walls is determined and stored as a captured attribute. This procedure may be continued for capturing additional dimensions, which may or may not be orthogonal. In yet other embodiments, the dimensions may be determined electrostatically.

In other embodiments, the dimension attributes are entered by a user. For example, a user may place the instrument on a grid with a scale indicated thereon. The user may then provide a visual estimation of the size of the instrument, based in part on the grid markings. The user may deliver this information to the system using a keypad, through voice recognition, or other equivalent mechanism. The user may add additional, readily discernible information, such as material type and instrument type. An exemplary voice command may be "Attributes: Stainless steel, forceps, length about 7 inches, width about 5 inches." The system may also be configured to account for variations in user-subjectivity and/or errors in user judgment.

Weight-Capture Device 206 is operable to capture a weight of a surgical instrument. In some embodiments, Weight Capture Device 206 may comprise a scale or similar device for capturing weight. Weight Capture Device 206 may provide a useful filter for automatically identifying, marking, and inventorying surgical instruments. Specifically, many instruments within a given surgical instrument type may have very similar appearances, including shapes, sizes, colors, etc. This may be particularly true when an instrument type is designed for a specific function where there may be little variation between instruments within the type because the function may prevent too much variation in form, i.e., size, shape, etc.

However, the weight of instruments within the instrument-type may not be constrained by the specific function. For this reason, Weight-Capture Device 206 may provide an accurate and quick method of identifying a surgical instrument that may otherwise be difficult.

Color-Capture Device 208 is operable to capture a color of the surgical instrument. In some embodiments, the color is determined by generating a beam of light, reflecting that beam off the surgical instrument, and then analyzing the wavelength of the reflected beam. In other embodiments, the color is determined by the image recognition software, wherein the software analyzes an image of the surgical instrument captured by Image Capture Device 202.

Material-Type Capture Device 210 is operable to determine the material of the device. Such materials may include stainless steel, silastic, ceramic, glass, titanium, plastic, and silicone, for example.

Surface-Type Capture Device 212 is operable to capture a surface quality of the surgical instrument. For example, a surgical instrument may be smooth, grooved, ridged, tracked, or include springs. In some embodiments, one or more of the foregoing surface qualities are captured. In further embodiments, additional surface qualities are examined.

In some embodiments, one or more of devices 202-212 are housed in a single apparatus. As will be readily understood by one of ordinary skill in the art, devices 202-212 need not be housed within the same apparatus. In some embodiments, devices 202-212 may be serially arranged, such as above and below a conveyor system for transporting the surgical instrument from one device to the next.

Returning again to FIG. 1 and System 100, Reference Database 106 stores one or more attributes for each of a plurality of surgical instruments. The database may be populated manually, using a capture module, or otherwise, as described in more detail later.

FIG. 3A illustrates a Reference Database 300 in accordance with an embodiment of the invention. Reference Database 300 stores attributes for a number of surgical instruments. The instruments are listed in the first column 302 of Reference Database 300. Reference Database 300 includes information on two attributes of each instrument, size and weight, listed in the second column 304 and third column 306, respectively. For each instrument, a corresponding size and weight are listed. For example, Instrument No. 2 has dimensions 2"×3" and a weight of 1.1 lbs.

Although Reference Database 300 is illustrated with two attributes, some embodiments may include one attribute or any number of attributes. Further, although the size in Reference Database is listed as an area, some embodiments may list a volume. In some embodiments, each dimension is listed, that is, the "Size" may be three separately-listed dimensions. Further, the attribute need not be a particular value and, in some embodiments, the attribute may be a range of values. For example, in one embodiment a range of weight is provided to accommodate different configurations or wear on the device over time. Similarly, some manufacturers' instruments may not be manufactured to the same weight each time and so a range of weights might be included to accommodate for the variances. In some embodiments, each size dimension is a range and may correspond to different configurations of a surgical instrument, such as open or closed. That is, Reference Database 300 may be structured to accommodate for the different configurations of a device when it is placed on the grid. Further, the dimensions might be sub-categorized to accommodate open and closed configurations. In this way, a user need not carefully place an instrument on the grid in a certain configuration in order to obtain an accurate identity. In some embodiments, the configuration of the device is determined by imaging software or is specified by a user.

FIG. 3B illustrates a Reference Database 320 in accordance with an embodiment of the invention. Reference Database 330 lists instruments according to their weight in the first column 322. Each weight corresponds to one or more reference instruments, listed in the second column 324. By capturing the weight of a surgical instrument, the identity of the instrument can be filtered. For example, an instrument weighing 0.9 lbs can be determined to correspond to Instrument i. On the other hand, an instrument weighing 1.1 lbs may correspond to either Instrument 2 or Instrument 4.

Similar to the description above with respect to FIG. 3A, Reference Database 320 may be structured in a variety of ways to accommodate a particular application or type of surgical instrument.

It should be noted that the attributes described above are offered for explanatory reasons only and are in no way intended to limit the scope of the invention. It should also be noted that the structure and resolution of the databases described herein are presented for explanatory purposes and alternative structures and resolutions may be used without deviating from the scope of the invention.

Returning again to FIG. 1 and System 100, Comparison Module 108 receives information from Capture Module 104 and Reference Database 106 and uses the information to determine a comparison score for the surgical instrument. In some embodiments, the Comparison Module 108 constructs a database query based on the attributes captured by the Capture Module 104. The database query may include multiple attributes. In some embodiments, the Comparison Module 108 then sends the database query to the Reference Database 106, which returns a list of candidate reference instruments and their attributes to the Comparison Module 108. The Comparison Module 108 then determines a comparison score by applying an algorithm to the attributes of the reference surgical instruments.

In some variations, a "score" is an arbitrary gradation of at least 10, 100, or 1000 degrees. By providing a gradation system, scores of multiple matches can be compared and ranked. A gradation system may include a scale from 0 to 100, such as a percentage scale.

Determining the comparison score may first include eliminating reference instruments that do not match. In this way, the resources necessary to determine a comparison score can be reduced. A first step may include identifying an instrument type associated with a subject instrument. In some embodiments, the instrument type is determined by identifying the outline of the instrument using edge detection analysis. This may be achieved using one or more cameras and comparing the images to the reference database. In other variations, the outline may be determined by lasers or other mechanisms, such as those described herein. In some embodiments, the system is trained to greatly reduce the number of potential matches when, for example, the instrument outline is relatively unique. For example, Army Retractors have a unique shape and outline while the outline of a hemostat could possibly cover dozens of different types of hemostats, some needle holders, and some scissors.

In addition, some variations may use the weight of the subject instrument to eliminate references instruments as potential matches. This may further include a weight variation that is specific to an instrument. For a given instrument type, a variation of a certain percentage may be acceptable as a potential match. For example, orthopedic chisels may lose 10% to 20% of their weight over the useful lifetime of the chisel because the sharpening process grinds off material from the chisel each time it is repaired. Other instruments (such as knife handles, hemostats, and ronguers the weight will be constant, or a smaller percentage, such as within +/−1%).

In some variations, other instrument features are used to eliminate potential matches. For example, determining the max length and width of the instrument (scanning with a laser, based on the outline of an image produced by a calibrated camera, etc.) can be used to eliminate potential matches.

In some variations, the imaging environment is controlled by calibrating the imaging equipment, such as the laser or camera. For example, by controlling the known parameters (light sources at known positions, cameras at known positions, cameras at known resolutions) a known object can be placed inside the imaging space and measured. By comparing the measured dimensions, shapes, and outlines of the object to the known dimensions, shapes, and outlines, the imaging system can be fine-tuned for improved to provide dimensions of an object or dimensions of features of the object. This may be an alternative to using a reference grid to determine instrument dimensions. For example, using calibrated cameras or calibrated lasers, a pixel size can be correlated with a physical size and the dimensions of an object can be determined by the number of pixels in the image of the object.

A second step in determining the comparison score may include calculating scores for different attribute classes. For example, the system may calculate one or more of an interior features score, an edge detection score, and an instrument weight score. The interior feature score may be determined by examining interior features of the instrument (position of nuts, bolts, hinges, grooves, logos, marks, etc.) from captured images. The interior features may be considered relative to the instrument outline and edges when determining an interior features score. The edge detection score may be calculated in a similar way—the outline and edge characteristics of the subject instrument are compared to the reference database and possible matches are given a score based on the similarity. Also, a weight score may be calculated based on the similarity of the weight of the subject instrument to the reference instruments. In other variations, other attributes are used to determine a score, such as any of the attributes captured in the methods and systems described herein.

A third step may be to assign weights to each of the scores calculated in step two. The weights may be apportioned according to the uniqueness an attribute is likely to offer. For example, a specific instrument type may include instruments of very similar outline, but very dissimilar interior features. The weights may be apportioned to account for this information. The weights may vary between instrument types. For example, the weights within a specific instrument type may not vary substantially (for example, when a weight is regulated by a hospital rule), but the outline may. In this scenario, the weight score may be weighted less than the edge detection score.

A fourth step may be to determine an aggregate score using the weighted attribute scores of the third step. The aggregate score may then be normalized to give a result within in the gradation system. This may be the comparison score.

Once the comparison score is determined, a series of thresholds may be used to provide a match or multiple potential matches. Above a certain threshold (for example above 95%) the system may be configured to declare a match. Between certain thresholds, the system may be configured to determine possible candidates for a match and may display the candidates to a user for their determination. In some variations, the range of thresholds is 85% and 95%. Below a certain threshold (for example, below 85%), the system may be configured to indicate that no match exists for any of the instruments stored in the reference databases. In this case, the system may offer the user the opportunity to add the instrument to the reference database.

Reference Database 106 may comprise a wide variety of instrument attributes, such as those described above with respect to Capture Device 200. The ability to reference a wide variety of attributes allows System 100 to distinguish between a plurality of similar surgical instruments. As discussed above, some instrument types may include instruments with only subtle differences in attributes. By including a variety of attributes in the identification process, System 100 may be attuned to discriminate based on one or more subtle differences. For example, if a range of dimensions is insufficient to uniquely identify a surgical instrument, it may be sufficient to reduce the number of possible candidate instruments. Then, a capture weight may be used to further refine the set of possible candidate instruments. In some embodiments, a given surgical instrument type may have a hierarchy of attributes that more easily distinguish between instruments within that type. For example, the type of a surgical instrument may be identified—automatically or user intervention—to be a scalpel and System 100 may then begin by capturing the attribute that is highest on the scalpel hierarchy, for example, weight. In this way, the efficiency of identification may be improved. It should be noted that the scalpel and weight correspondence is given by example only, and a scalpel, or any other instrument, may have any hierarchy of attributes.

The Exporting Module 110 exports the comparison scores generated by the Comparison Module 108. In some embodiments, the comparison scores may be exported to a display, such as a dedicated computer or a mobile device. In other embodiments, the comparison scores are exported to another module which determines whether one or more of the comparison scores indicate a match in the Reference Database 106, as described in more detail later. In some cases, the differences between reference instruments may be insufficient to accurately identify the target instrument to a predetermined degree of certainty, in which case a comparison score for each reference instrument above a threshold may be provided to a user, as described in more detail later.

In some embodiments, system 100 may be a single apparatus. In other embodiments, system 100 may comprise one or more separate and distinct apparatuses. In some embodiments, the surgical instruments may be fed into an input of a single device, such as a hopper or the beginning of a conveyor belt. In other embodiments, the camera may be housed inside the ceiling of a room and focused upon a particular spot. For example, the particular location may be a table upon which surgery trays are maintained. In this way, the systems and methods described herein can create a record of those instruments which are used and not used by surgeons during an operation.

In some embodiments, the respective functions of the components of system 100 are centrally controlled by a processor (not shown). The processor may instruct the Capture Module 104 to capture at least one attribute of the surgical instrument, may instruct the Comparison Module 106 to send a query to the Reference Database 106, or provide any of the other functions described with reference to FIG. 1.

Figure 4:
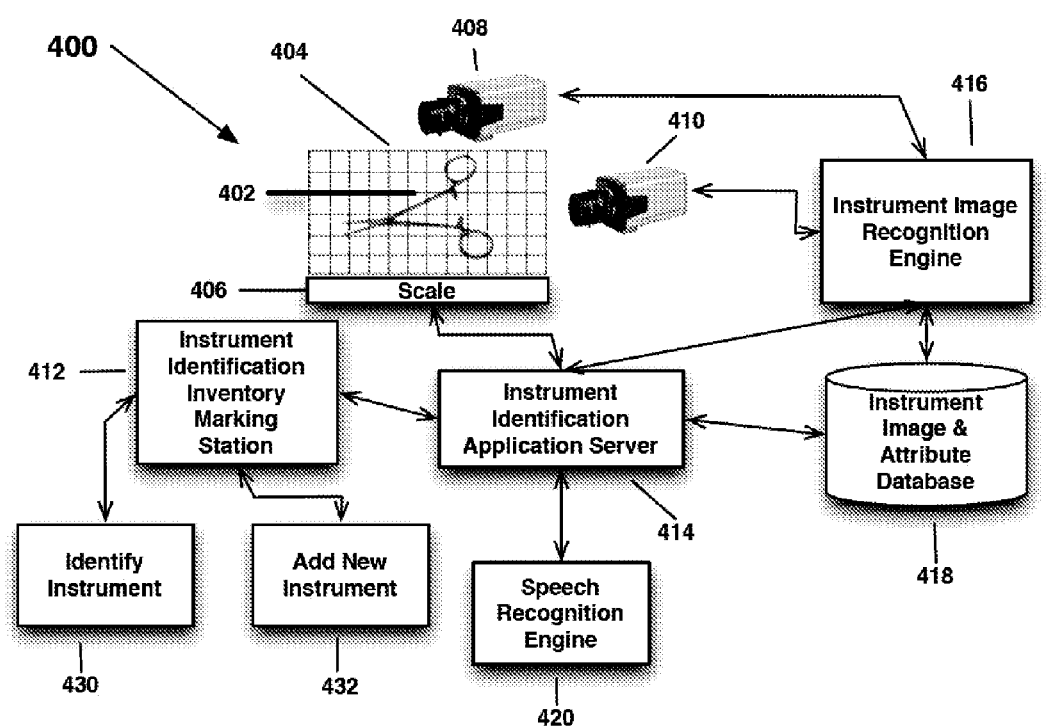
FIG. 4 is a schematic diagram of an exemplary system for automatic identification of a surgical instrument, in accordance with an embodiment of the invention.

FIG. 4 is a schematic diagram of an exemplary System 400 for automatic identification of a Surgical Instrument 402, in accordance with an embodiment of the invention. Elements of System 400 may correspond to elements of System 100 described above with respect to FIG. 1. System 400 includes a Grid 404, a Scale 406, Cameras 408 and 410, an Instrument Identification, Inventory, and Marking Station 412, an Instrument Identification Application Server 414, an Instrument Image Recognition Engine 416, an Instrument Image and Attribute Database 418, and a Speech Recognition Engine 420. Instrument Identification, Inventory, and Marking Station 412 further includes an Identify Instrument Module 430 and an Add New Instrument Module 432.

In some embodiments, a Surgical Instrument 402 is placed on a background containing a regularly spaced Grid 404. The grid lines may be used to determine the dimensions of the instrument. For example, Grid 404 may comprise lines every centimeter, as discussed above. Grid 404 allows for bounds to be placed on the length and width of the instrument. The length and width bounds may be used to restrict image comparisons to only instruments with similar length and width attributes as stored in the Instrument Image & Attribute Database 418. A Scale 406 may optionally be used to further restrict image comparisons to only images with a similar weight attribute as stored in the Instrument Image & Attribute Database 418. An identification request activates the scale causing it to capture the instrument weight and to pass it to the Instrument Identification Application Server 414. The system may include one or more Cameras 408 and 410 to capture instrument images for image comparison purposes.

The Instrument Identification, Inventory, and Marking Station 412 may be used with the Identify Instrument Component 430 of the Station 412 to recognize, capture and initiate all instrument identification requests. An instrument identification request can be initiated, for example by: a keyboard request (keystrokes or menu selections); a touchscreen request (keystrokes or menu selections); a footswitch request; a mouse, touchpad (or other switch) for menu selections; or a speech command request routed to the Speech Recognition Engine 420. In some embodiments, System 400 is operable to accept a request by some or all of the foregoing.

In some embodiments, the identification request(s) also contains instrument attribute information that is used to restrict the number of instrument image comparisons. For example, an instrument identification request may include an instrument category ("Retractor," for example), an instrument sub-category ("Malleable," for example), and instrument material type ("Stainless Steel," for example). In this way, a user may provide information to focus or supplement the database query. Thus, System 400 may capture one or more images using the one or more Cameras 408 and 410 and compare the image(s) only to reference image(s) of malleable, stainless steel retractors with similar weight, length and width attributes, thereby increasing the efficiency and accuracy of the identification system. The additional instrument attributes can be provided, for example, by: a keyboard request (keystrokes or menu selections); a touchscreen request (keystrokes or menu selections); a mouse, touchpad, or other switch for menu selections; or a speech command request routed to the speech recognition engine 420. In some embodiments, System 400 is operable to accept a request by some or all of the foregoing.

System 400 may also be used for storage tracking, storage, and maintenance of surgical instruments. For example, Instrument Identification, Inventory, and Marking Station 412 may be configured to maintain a record of when and where the surgical instruments have been identified. The record may include the last time the instrument was identified, thereby providing an estimate of the instrument's location in the hospital (e.g., in storage, in surgery kit, in decontamination, in assembly, in sterilization, etc.). The record may also include the number of times the instrument has been used, which may facilitate maintenance scheduling or repair scheduling. In other embodiments, a collection of instruments in a sterile collection department may be sorted and verified to ensure they are the same instrument, prior to collective sterilization and bagging by a technician. In such embodiments, Instrument Image & Attribute Database 418 may also include manufacturer's recommended maintenance intervals for an identified surgical instrument. This can be used to send alerts to technicians to plan maintenance procedures accordingly. Further, the Instrument Image & Attribute Database 418 may be continually updated to include current information on the available surgical instruments in an instrument type. Thus, when a surgical instrument is identified as in need of replacement, System 400 can notify a user of a specific replacement instrument (i.e., manufacturer and model no.) that is preferred because of quality or price, for example. In some embodiments, System 400 may automatically order the desired replacement instrument. Instrument Image & Attribute Database 418 may also include manufacturer specific information that assists in the purchasing decision for replacement instruments. Such information may include instruments' catalog numbers, current and historical prices, instrument description, cross-referenced products, etc.

In some embodiments, the systems and processes described herein are used on a conveyor belt system which transfers an instrument from and to the various components. For example, an identified instrument may be transferred to a marking station or a bagging station via the conveyor belt. An instrument with no match or multiple matches may be transferred to a manual intervention station where a user determines the identity of the instrument. In other embodiments, the conveyor belt system may be used to assemble surgical kits. For example, an identified surgical instrument may be routed to a particular location for inclusion in a predetermined kit. Additional instruments from the kit may also be routed to that same location. Once the surgical kit has been assembled, System 400 may notify a user that the kit is ready to be used. In some embodiments, the surgical instruments may be routed to a peel-pack labeling system. For example, System 400 may route the identified surgical instrument to a peel-pack station which also adds an identification label to the package.

Instrument Image & Attribute Database 418 may also include modules for improving management of surgical instruments. In some embodiments, a record may be maintained of the surgeries (surgery type, patient, date, etc.) in which an individual instrument was used. This may, for example, facilitate better controlling of the spread of infectious disease. In such an embodiment, when a patient develops an infection from a surgery, any instruments used in that surgical procedure can be tracked and identified and the decontamination and sterilization history and procedures for the instruments can be examined. Further, any other patients which were operated on with the same instrument can be identified and a follow-up can be performed to limit the spread of an instrument-related infectious disease.

Figure 5:
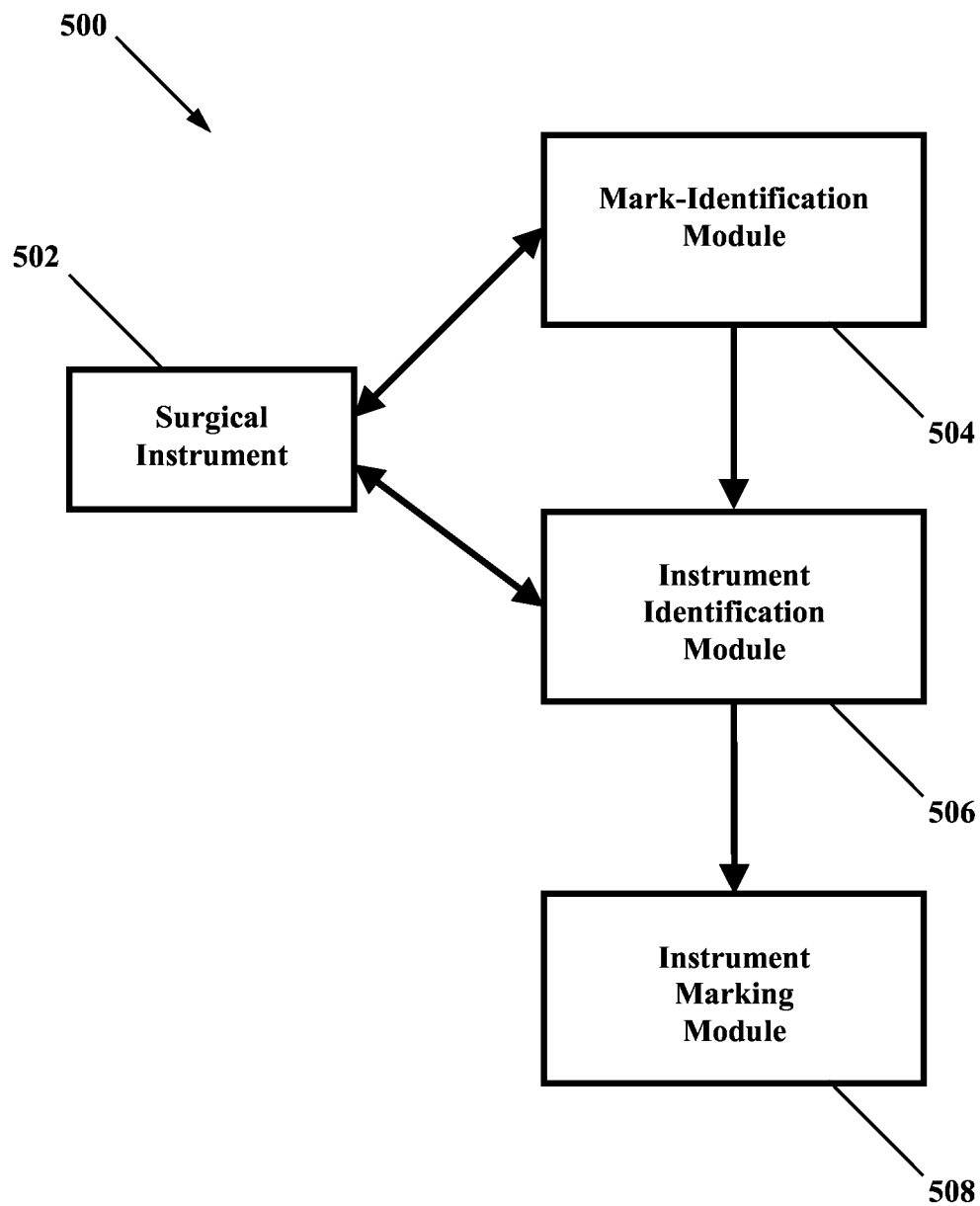
FIG. 5 is a block diagram of an exemplary system for identifying and marking a surgical instrument, in accordance with an embodiment of the invention.

FIG. 5 is a block diagram of an exemplary System 500 for identifying and marking a Surgical Instrument 502, in accordance with an embodiment of the invention. System 500 includes Mark-Identification Module 504, Instrument Identification Module 506, and Instrument Marking Module 508.

As referred to herein, a "mark" on a surgical instrument can be understood to mean an identification "tag" or other mechanism added to a surgical instrument for the purposes of identifying that instrument. In some embodiments, the mark serves no surgical purpose and is solely added for identification purposes. Such marks may include, for example, a Radio Frequency ID ("RFID") tag, a barcode, an alphanumeric identifier, or other identifying features. In some embodiments, the mark may be generated by etching a pattern or other identifying feature onto the surgical instrument. Such etching techniques may include laser-etching, ball peen etching, chemical etching, and/or any etching technique capable of creating a pattern or other identifying feature on the surgical instrument.

Mark Identification Module 504 may include a device configured to interact with or otherwise identify a mark added to a surgical instrument. For example, if the mark were an RFID tag, the Mark Identification Module 504 may include a device configured to emit an electromagnetic field, which causes an RFID tag to transmit identifying data. In the event that an RFID tag is detected on the surgical instrument, the Mark-Identification Module 504 may notify the Instrument Identification Module 506 that no identification is necessary. If no RFID tag is detected, the Mark-Identification Module 504 may notify the Instrument Identification Module 506 that an identity of the surgical instrument is needed.

The ability to uniquely identify specific surgical instruments is the key to many perioperative optimization opportunities. To uniquely mark an instrument, it may be helpful to first identify the instrument. Once marked, the System 500 may update (not shown) a reference database (shown) to include the identifying mark for later reference.

Instrument Identification Module 506 may comprise any of the systems and methods for identifying a surgical instrument that are discussed herein. Once the identity of the surgical instrument is determined, Instrument Identification Module 506 transmits that identity to the Instrument Marking Module 508.

Instrument Marking Module 508 may comprise any device configured to generate or add an identifying mark to a surgical instrument. In some embodiments, the Instrument Marking Module 508 generates an identification mark which is manually applied to the surgical instrument. In other embodiments, the Instrument Marking Module 508 may also be operable to attach the mark to the instrument. In yet other embodiments, the Instrument Marking Module 508 may be operable to etch a pattern or other identifying feature onto the surgical instrument.

Figure 6:
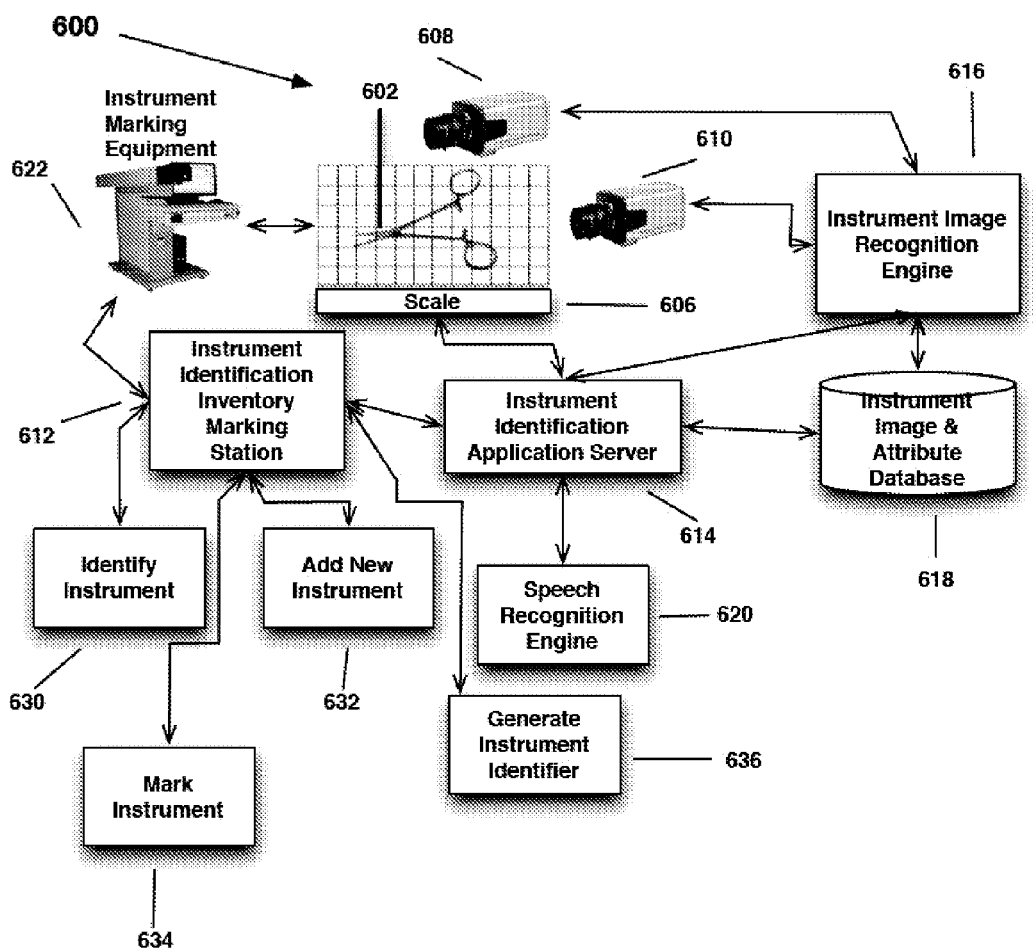
FIG. 6 is a schematic diagram of an exemplary system for automatic identification and marking of a surgical instrument, in accordance with an embodiment of the invention.

FIG. 6 is a schematic diagram of an exemplary System 600 for automatic identification and marking of a surgical instrument 602, in accordance with an embodiment of the invention. System 600 includes a Grid 604, a Scale 606, Cameras 608 and 610, an Instrument Identification, Inventory, and Marking Station 612, an Instrument Identification Application Server 614, an Instrument Image Recognition Engine 616, an Instrument Image and Attribute Database 618, a Speech Recognition Engine 620, and an Instrument Marking Equipment 622. Instrument Identification, Inventory, and Marking Station 612 further includes an Identify Instrument Module 630, an Add New Instrument Module 632, a Mark Instrument Module 634, and a Generate Instrument Identifier Module 636.

Some elements of System 600 may correspond to elements of System 400 described above with respect to FIG. 4. To the extent some elements are repeated, a description of their functionality is not repeated in the following description of System 600.

The Mark Instrument component 634 of the Instrument Identification, Inventory, and Marking Station 612 may provide functionality to assist in identifying and marking surgical instruments. The ability to uniquely mark and identify a specific instrument enables many important processes in the perioperative environment. Unique instrument identification makes possible at least the following: tracking individual instruments to maintain scheduled maintenance; tracking usage of specific instruments for infection control and other patient safety related issues; associating specific instruments to defined collections with known locations (for example, instrument sets, peel packs, and peg boards); tracking usage history of specific instruments; maintaining precise instrument inventories; tracking the root causes of instrument loss as well as tracking instrument theft; maintaining instrument sterilization, maintenance and repair history; and tracking the location and status of an instrument at any point in the perioperative process.

System 600 provides the following functionality to support (or to drive) the instrument marking process: identify the instrument; generate a unique identifier for the instrument using the Generate Instrument Identifier 636 of the Instrument Identification, Inventory, and Marking Station 612; pass the unique instrument identifier to the Instrument Marking Equipment 622; and mark the instrument with the generated unique instrument identifier.

With respect to generating a unique identifier, each HCO may initially set up the "identifier profile." For example, this may include: facility code, mark (or purchase) date and sequential or randomly generated unique identifiers. Each of these components may be based off a HCO specified length and format. The end result would be a unique ID generated for each instrument prior to marking.

In some embodiments, passing the unique identifier to the Instrument Marking Equipment 622 is achieved through an interface from the Instrument Identification, Inventory, and Marking Station 612 to the Instrument Marking Equipment 622. In other embodiments, it is achieved by manually entering the unique instrument identifier into the user interface of the Instrument Marking Equipment 622.

Figure 7:
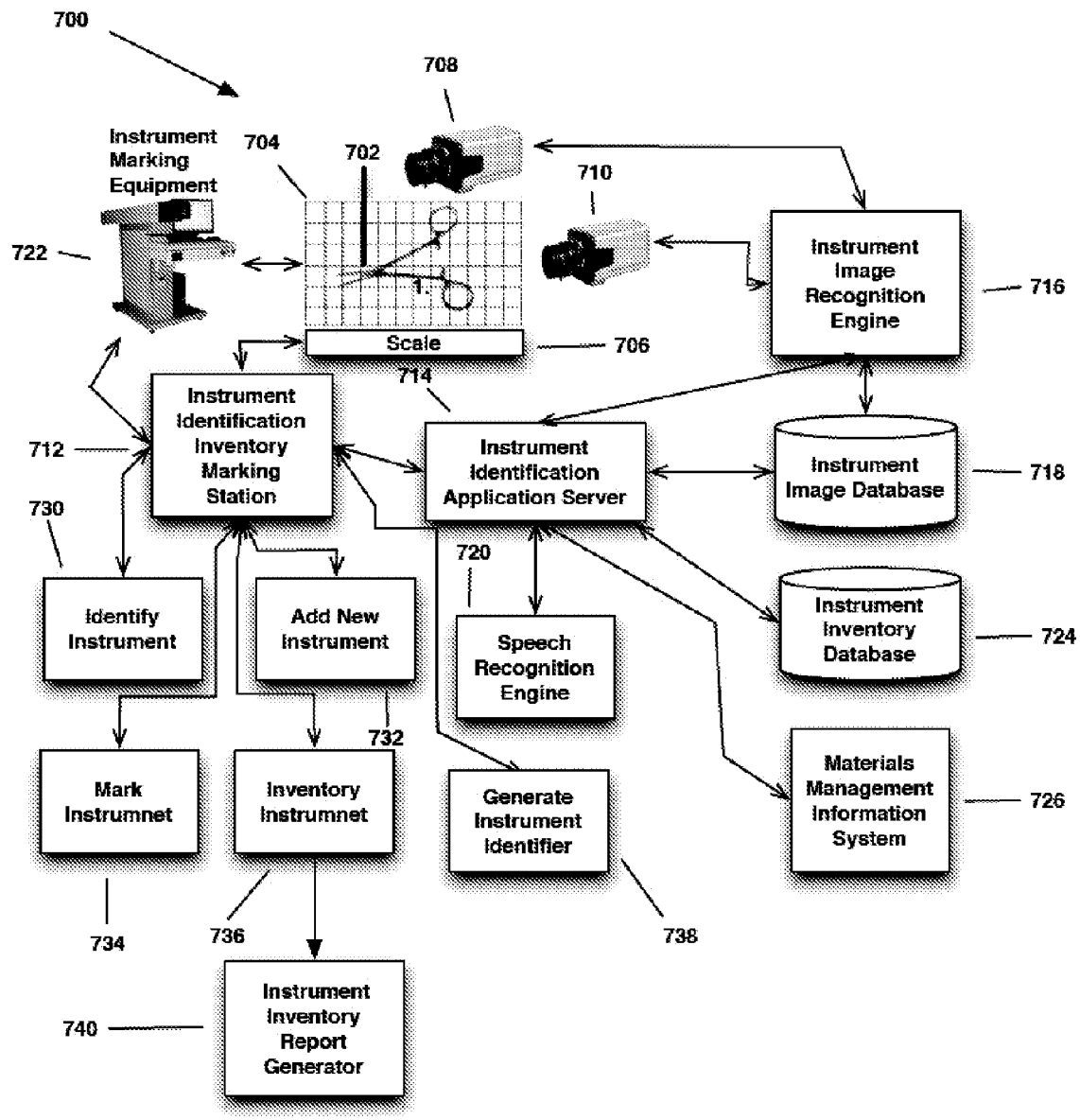
FIG. 7 is a schematic diagram of an exemplary system for automatic identification, marking, and inventorying of a surgical instrument, in accordance with an embodiment of the invention.

FIG. 7 is a schematic diagram of an exemplary System 700 for automatic identification, marking, and inventorying of a Surgical Instrument 702, in accordance with an embodiment of the invention. System 700 includes a Grid 704, a Scale 706, Cameras 708 and 710, an Instrument Identification, Inventory, and Marking Station 712, an Instrument Identification Application Server 714, an Instrument Image Recognition Engine 716, an Instrument Image and Attribute Database 718, a Speech Recognition Engine 720, an Instrument Marking Equipment 722, an Instrument Inventory Database 724, and a Materials Management Information System 726. Instrument Identification, Inventory, and Marking Station 712 further includes an Identify Instrument Module 730, an Add New Instrument Module 732, a Mark Instrument Module 734, a Generate Instrument Identifier Module 736, an Inventory Instrument Module 738, and a Generate Instrument Inventory Report Module 740.

Some elements of System 700 may correspond to elements of System 600 described above with respect to FIG. 6. System 700 builds on System 600 by adding an inventorying system. Once an instrument is marked, it may be useful to store the unique instrument information in a database. To the extent some elements are repeated in System 600, a description of their functionality is not repeated in the following description of System 700.

The steps in the identification, marking, and inventory process of System 700 may be: identify the instrument type, generate a unique instrument identifier, mark the instrument with the unique identifier, and record the unique identifier and associate it with the instrument in the Instrument Inventory Database 724. In some embodiments, the instrument marking process will be part of an instrument inventory process, but an instrument inventory process can be conducted independently of instrument marking.

If instruments are marked, the Instrument Inventory Database 724 contains a record of each instrument identifier and the associated instrument type along with a count for the total number of instruments for each specific instrument type. The Instrument Image and Attribute Database 718 contains reference images for the instrument type. It also contains attribute data and manufacturer information associated with the instrument type. The attribute data contains but is not limited to: instrument category, instrument sub-category, manufacturer, material, color, length, width, height and instrument surface data (groove, cutting, flat, teeth, etc.). The manufacture data may include but is not limited to usage/maintenance/repair instructions, product descriptions, additional product images, and part or catalog numbers. The Instrument Inventory Database 718 may also contain instrument purchase price data as collected from interfaces to the HCO's Materials Management Information System 726.

In some embodiments, all instruments are marked, but in some embodiments only some of the instruments are marked. In this situation, the Instrument Inventory Database 724 may contain a count of the number of instances of each specific instrument type.

System 700 will use the Inventory Instrument component 734 of the Instrument Identification, Inventory, and Marking Station 712 to support instrument inventory operations. Instrument inventory process steps may include: Initiate Instrument Inventory Request, Identify the Instrument, Generate an instrument inventory report as needed by using the Instrument Inventory Report Generator 740. With respect to identifying the instrument, if the instrument is already marked, System 700 may associate the instrument type with the unique instrument identifier and increment the count of instances of the specific instrument type. In some embodiments, System 700 may update the inventory maintained in a third party materials management system (or third party inventory system).

Figure 8:
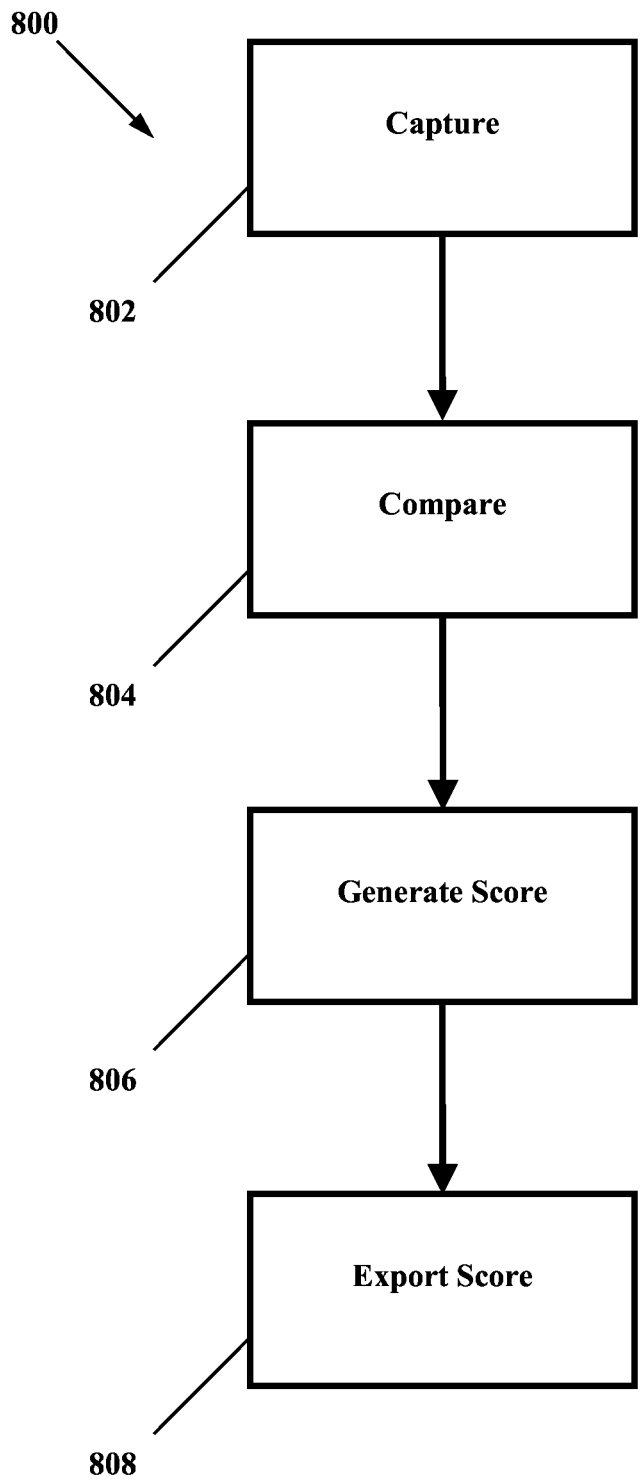
FIG. 8 is a flow diagram of an exemplary process of identifying a surgical instrument, in accordance with an embodiment of the invention.

FIG. 8 is a flow diagram of an exemplary Process 800 of identifying a surgical instrument, in accordance with an embodiment of the invention. Process 800 includes Capturing 802 at least one attribute of the surgical instrument, Comparing 804 the at least one captured attribute to at least one attribute of a plurality of reference instruments, Generating 806 a comparison score for the surgical instrument, and Exporting 808 the comparison score.

Capturing 802 at least one attribute of the surgical instrument may include any of the methods described in this disclosure. In some embodiments, capturing at least one attribute includes one or more of capturing an image of the surgical instrument, a dimension of the surgical instrument, a weight of the surgical instrument, a color of the surgical instrument, a material-type of the surgical instrument, and a surface-type of the surgical instrument. In further embodiments, capturing at least one attribute may include capturing multiple dimensions of the surgical instrument. In other embodiments, capturing an image may include capturing multiple images of a surgical instrument. An image may be analyzed to determine the size and/or shape of a feature of the instrument, such as the teeth and/or handle of the instrument.

Comparing 804 the at least one attribute may include comparing the attribute captured in Capturing step 802 to attributes of a plurality of reference instruments stored in an attribute database. Comparing 804 may comprise constructing a database query (based on the captured instrument attributes) for the attribute database. The queries may be used to filter the number of comparisons, based upon the captured attributes, and produce a set of candidate reference instruments.

Generating 806 a comparison score for the surgical instrument may be based on Comparing 804 the at least one captured attribute to the at least one stored attribute of a plurality of reference instruments. The comparison score is an indication of the likelihood that the instrument corresponds to a given instrument in the attribute database. Multiple comparison scores may be generated if multiple reference instruments are produced by Comparing step 804.

Exporting 808 may comprise exporting the comparison score to a display for a user to review the results of the comparison. In some embodiments, Exporting 808 includes sending the results to an additional module for determining whether the comparison score exceeds a threshold value, as explained below with respect to FIG. 9.

Figure 9:
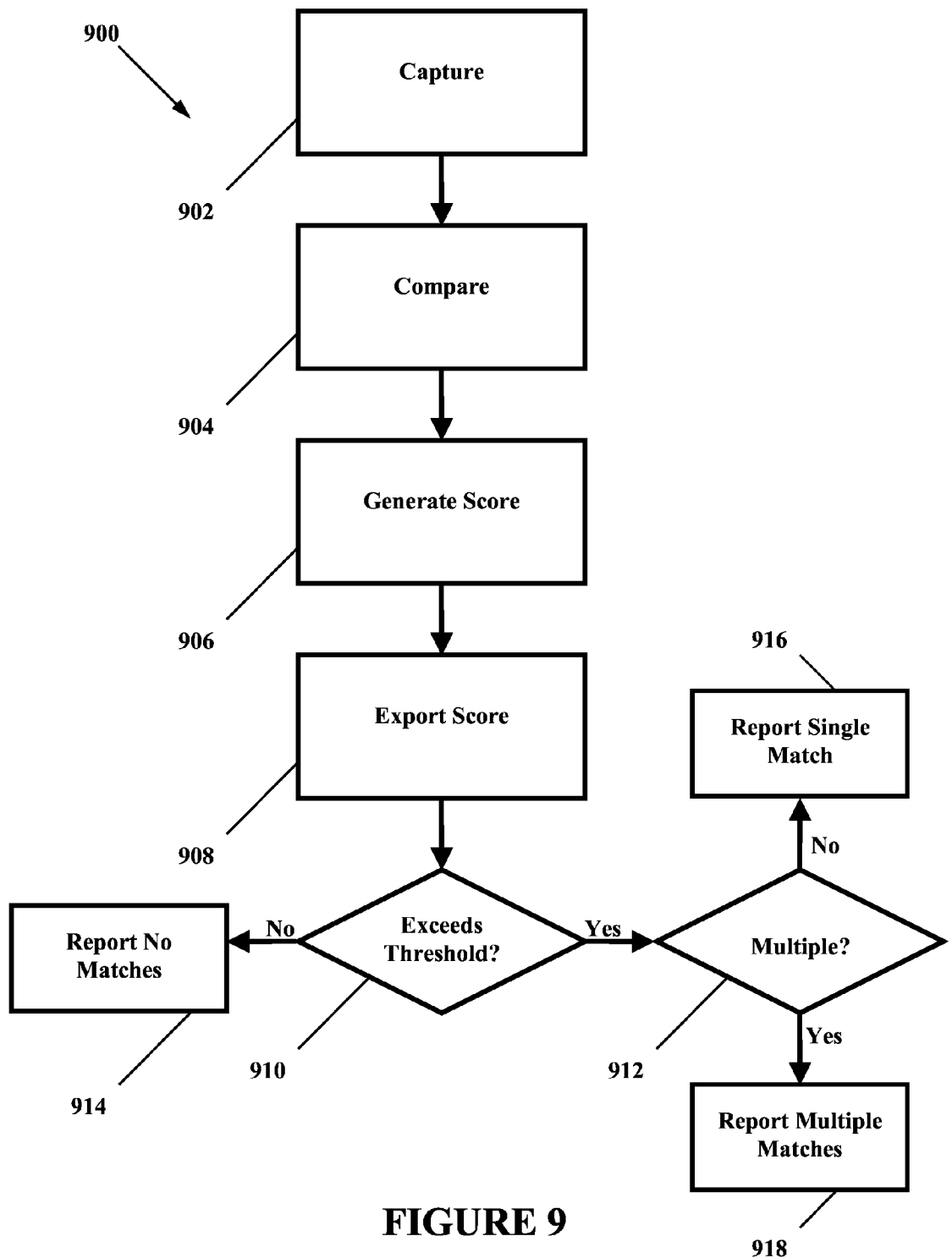
FIG. 9 is a flow diagram of an exemplary process of identifying a surgical instrument, in accordance with an embodiment of the invention.

FIG. 9 is a flow diagram of an exemplary Process 900 of identifying a surgical instrument, in accordance with an embodiment of the invention. Process 900 includes Capturing 902 at least one attribute of the surgical instrument, Comparing 904 the at least one captured attribute to at least one attribute of a plurality of reference instruments, Generating 906 a comparison score for the surgical instrument, Exporting 908 the comparison score, determining whether the comparison score Exceeds a Threshold 910, determining whether Multiple 912 comparison scores exceed the threshold, and Reporting 914, 916, and 918 the results of the determinations.

Some steps of Process 900 may correspond to steps of Process 800 described above with respect to FIG. 8. Process 900 builds on Process 800 by determining whether one or more comparison scores exceed a threshold for determining a match. To the extent some elements are repeated in Process 800, a description of their functionality is not repeated in the following description of Process 900.

Decision 910 determines if there are any comparison scores which exceed a threshold value. If there are no such comparison scores, Process 900 Reports that there are No Matches 914. If there is at least one such comparison score, Process 900 then determines whether there are Multiple Matches 912. If there are not Multiple Matches, Process 900 Reports that there is a Single Match 916. If there are Multiple Matches, Process 900 Reports that there are Multiple Matches 918.

The determination 910 of whether a comparison score exceeds a threshold may be controlled by the HCO or a user. For example, the threshold value may be changed based on such parameters as: the likelihood of a false match, the number of similar instruments, the risk associated with a false match, etc.

When no comparison score exceeds the threshold, Process 900 then reports that no matches are made. A "No Match" result may indicate that the instrument needs to be manually identified. In the event of a "No Match" result, Process 900 may include an additional step (not shown) of adding a new instrument to the attribute database.

In some embodiments, adding a new instrument process includes capturing at least one attribute of the new instrument. In further embodiments, the process offers a menu driven, form-based data entry capabilities for attribute information. Further embodiments may allow importing of manufacturer instrument information. Some embodiments may provide for testing of the system by attempting to identify an example of instrument of the same type as the new instrument. In addition, the adding a new instrument process may allow for adding and deleting reference images associated with a specific instrument type already contained in the Instrument Image & Attribute Database. Adding a new instrument may also include creating, reading, and updating operations on the attributes and manufacturer information associated with a specific instrument type already contained in a reference database. Note that the adding a new instrument process can be used with any of the embodiments described herein.

If at least one comparison score exceeds the threshold, Process 900 then determines 912 whether there are multiple matches. If there are multiple matches, Process 900 may include an additional step (not shown) of displaying the instrument image along with the multiple reference images (each tagged with manufacturer information (instrument name, manufacturer, category, sub-category, instrument part number, and manufactured product identifier (catalog number))). Process 900 may include a further additional step (not shown) where a user can select one of the references images as the match or declare that none of the reference images match. If one of the results is selected as a match then Process 900 may display the instrument image along with the multiple reference images (each tagged with manufacturer information (instrument name, manufacturer, category, sub-category, instrument part number, and manufactured product identifier (catalog number))). If one of the results is selected as a match then Process 900 may include an additional step to update the attribute database with the instrument image along with the multiple reference images (each tagged with manufacturer information (instrument name, manufacturer, category, sub-category, instrument part number, and manufactured product identifier (catalog number)).

If a single match is determined 912, then Process 900 Reports the Single Match 916. Process 900 may include an additional step (not shown) of displaying the instrument image, matched reference image and associated instrument information (instrument name, manufacturer, category, sub-category, instrument part number, and manufactured product identifier (catalog number)). In some embodiments, Process 900 may reference (not shown) manufacturer instrument maintenance, instrument repair, and instrument usage instructions in an additional database.

Figure 10:
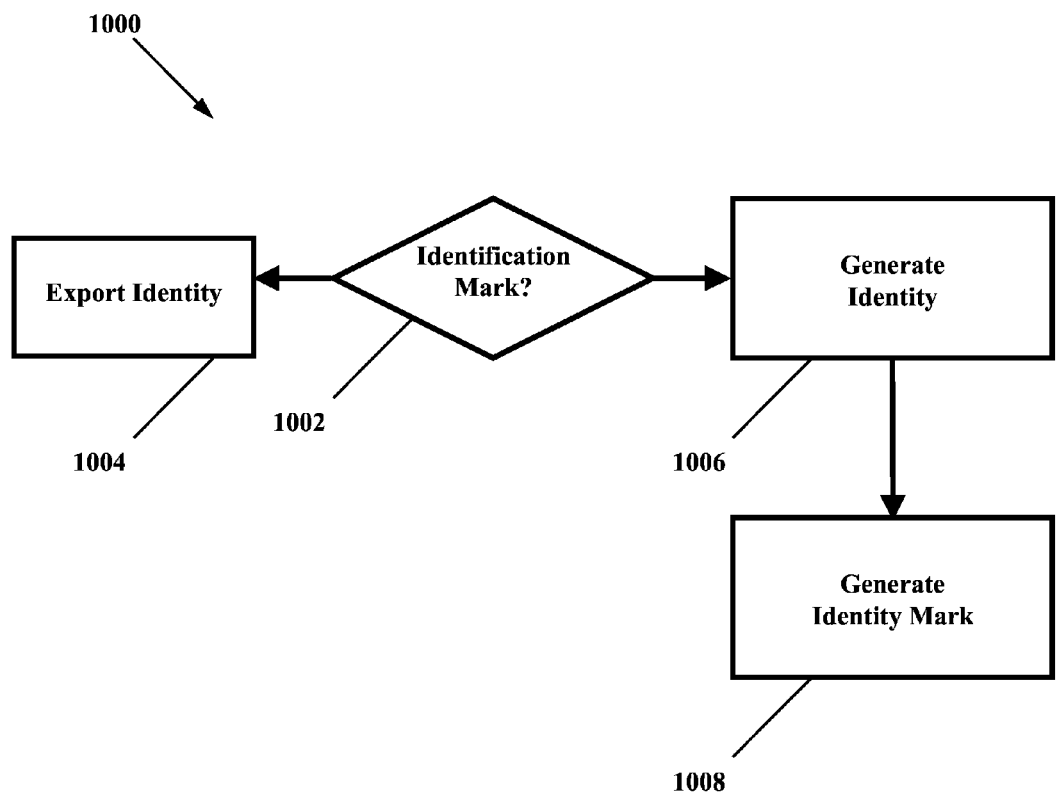
FIG. 10 is an exemplary process of generating an identity marking for a surgical instrument, in accordance with an embodiment of the invention.

FIG. 10 is an exemplary Process 1000 of generating an identity marking for a surgical instrument, in accordance with an embodiment of the invention. Process 1000 begins with a determination 1002 of whether the surgical instrument already includes an identification mark. If the determination is "Yes," the process Exports the Identity 1004 and the process ends. If the determination is "No," the process Generates an Identity 1006 for the surgical instrument. The identity of the surgical instrument may be generated using any of the process described herein for identifying a surgical instrument. Once an identity is generated, the process then Generates an Identity Mark 1008, which may be added to the instrument using any of the process described herein for marking a surgical instrument.

Figure 11:
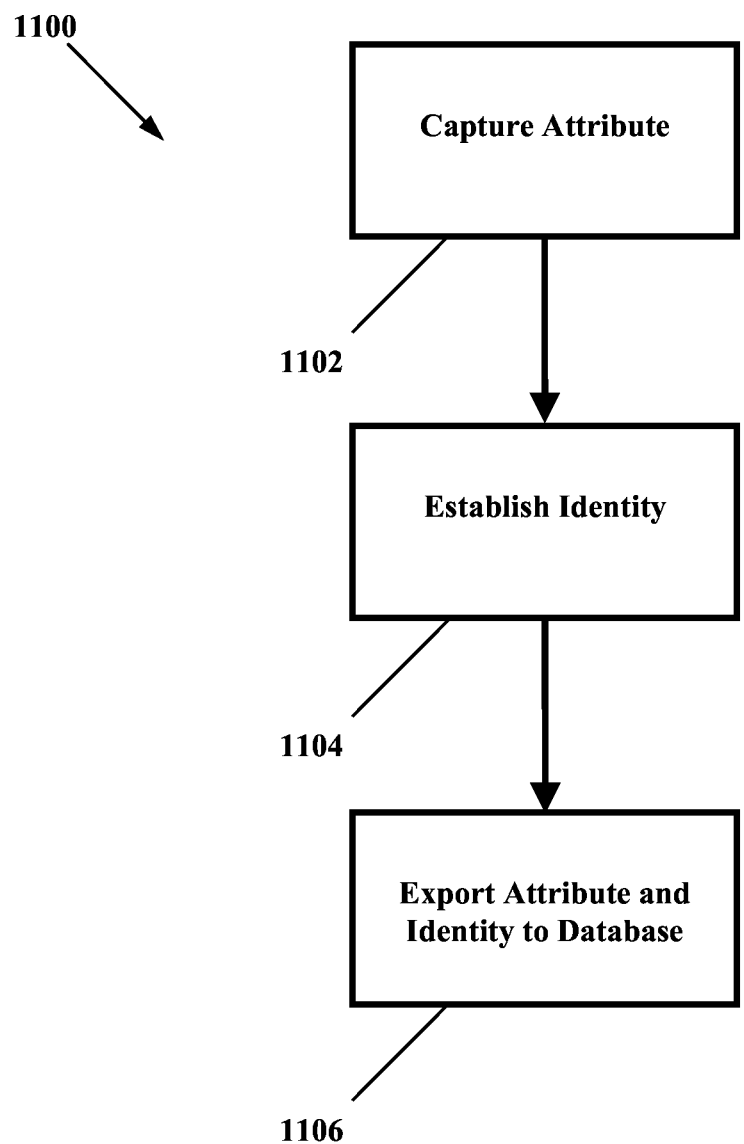
FIG. 11 is an exemplary process of building a database of at least one attribute of a plurality of surgical instruments, in accordance with an embodiment of the invention.

FIG. 11 is an exemplary Process 1100 of building a database of at least one attribute of a plurality of surgical instruments, in accordance with an embodiment of the invention. Process 1100 begins by Capturing an Attribute 1102 of the surgical instrument. Once at least one attribute is captured, Process 1100 then Establishes an Identity of the Instrument 1104. The identity may be established by a manual input, by accessing a manufacturer's website, or by accessing another database. Other methods may also be used for establishing the identity without deviating from the scope of the invention. Once the at least one attribute is captured and the identity is established, both are Exported to a Database 1106.

In some embodiments, the systems and methods described herein can be used to automatically identify other hospital objects, medical equipment and medical devices, such as orthopedic pins, screws, and plates.

In some embodiments, the attribute information stored in a reference database, such as those described herein, may be accessed remotely, via a mobile device (including, but not limited to, medical devices with integrated or connected cameras and barcode scanners), for example. In such a scenario, the information stored in the reference database may be used for training purposes. For example, trainee technicians may use the mobile device to verify the identity of an instrument. In other embodiments, the attribute information may be used to certify a technician by, for example, providing a series of images of reference instruments for the technician to identify. In some embodiments, the information stored in the reference database may be used to identify a surgical instrument without using a module to capture an attribute of the device. For example, a user may indicate that an instrument is a "Retractor, Malleable, Stainless Steel, and less than 10 inches." A number of candidate images may then be presented to the user to determine a match. In some embodiments, a user may use a mobile device to access the Reference Database and obtain recommended procedures or maintenance for an instrument.

Some exemplary advantages of embodiments of the invention described herein include: using image recognition to automate instrument identification; using speech recognition to automate attribute capture and attribute based instrument searches; building taxonomy of instrument categories and sub-categories with an associated set of attributes and using this taxonomy and attributes to reduce the search space for the image recognition system; applying automated instrument recognition to facilitate the instrument marking and instrument inventory processes; and combining, image recognition, instrument physical properties and instrument attributes to automate identification. Other advantages not listed above will be readily apparent to those of ordinary skill in the art.

Some embodiments may be operable to recognize multiple instruments at a time (over-lapping and non-over-lapping). Such embodiments may be used to determine which instruments on an instrument tray are used by surgeon during a procedure. This information may further be used to determine which "surgery tray kit" is appropriate for which surgeon. A surgery tray kit may include a number of surgical instruments, where one kit differs from the other by the type or number of instruments in a kit.

In some variations, the use of a surgery tray kit can be exploited to reduce the number of potential matches. For example, if a count sheet includes a specific itinerary of instruments, then the system may be programmed to only compare reference instruments listed on the itinerary sheet. This may greatly reduce the resources necessary to search the reference database. Further, this may enable the system to determine which instruments have been used during a surgery when they are placed in for example, an instrument tray, back table, or a dirty instrument bowl after use. This may further allow for identifying overlapped instruments, where only partial images are available. Although partial images may be impractical or ineffectual to search the entire reference database, such partial images may be sufficient when the universe of potential matches has been limited by a count sheet.

Some embodiments may be operable to recognize multiple instruments in clear liquids.

As will be readily understood by those of ordinary skill in the art, individual features of the above apparatuses and methods may be interchangeable and, in some embodiments, may be selected to tailor a particular system to a predetermined instrument type. For example, a material-type capture device may be configured to distinguish only between stainless steel and titanium where other material types are not typically used.

In some embodiments, one or more of the systems and methods described herein is used in conjunction with a portable electronic device. In one such embodiment, a doctor, a nurse, or other field personnel may use a camera, voice recognition, and/or keyboard functionality of a portable electronic device to input one or more attributes of a surgical instrument. In a further embodiment, the portable electronic device may have installed a computer program that incorporates one or more of the surgical instrument identification modules described, such as, but not limited to, an instrument identification application server and an instrument image & attribute database. In other embodiments, the portable electronic device may communicate with a separate instrument identification server and provide the captured instrument attributes. The server may then provide the identity of the instrument, a matching score, or other information described above. In addition, the server may provide instrument repair history, repair and maintenance procedures, usage information, or any other information available that is related to the surgical instrument.

In some embodiments, the steps of a method or algorithm described in connection with the embodiments disclosed herein may be embodied directly in hardware, in firmware, in a software module executed by a processor module, or in any practical combination thereof. A software module may reside in computer-readable storage, which may be realized as RAM memory, flash memory, ROM memory, EPROM memory, EEPROM memory, registers, a hard disk, a removable disk, a CD-ROM, or any other form of storage medium known in the art. In this regard, a computer-readable storage may be coupled to processor module such that the processor module can read information from, and write information to, computer-readable storage. As an example, a processor module and a computer-readable storage may reside in their respective ASICs. The computer-readable storage may also be integrated into the processor module. In one embodiment, the computer-readable storage may include a cache memory for storing temporary variables or other intermediate information during execution of instructions to be executed by processor module. The computer-readable storage may also include non-volatile memory for storing instructions to be executed by processor module.

The computer-readable storage may include an attribute database in accordance with one or more exemplary embodiments of the invention. Attribute databases may be configured to store, maintain, and provide data as needed to support the functionality of automatic identification, marking, and inventorying of surgical instrument. Moreover, an attribute database may be a local database coupled to processor module, or may be a remote database, for example, a central network database, and the like. An attribute database may be configured to maintain, without limitation, surgical instrument attributes as described herein. In this manner, an attribute database may include a lookup table for purposes of storing surgical instrument parameters.

Although the present invention has been fully described in connection with embodiments thereof with reference to the accompanying drawings, it is to be noted that various changes and modifications will become apparent to those skilled in the art. Such changes and modifications are to be understood as being included within the scope of the present invention as defined by the appended claims. The various embodiments of the invention should be understood that they have been presented by way of example only, and not by way of limitation. Likewise, the various diagrams may depict an example architectural or other configuration for the invention, which is done to aid in understanding the features and functionality that can be included in the invention. The invention is not restricted to the illustrated example architectures or configurations, but can be implemented using a variety of alternative architectures and configurations. Additionally, although the invention is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the invention, whether or not such embodiments are described, and whether or not such features are presented as being a part of a described embodiment. Thus the breadth and scope of the invention should not be limited by any of the above-described exemplary embodiments.

In this document, the term "module" as used herein, refers to software, firmware, hardware, and any combination of these elements for performing the associated functions described herein. Additionally, for purpose of discussion, the various modules are described as discrete modules; however, as would be apparent to one of ordinary skill in the art, two or more modules may be combined to form a single module that performs the associated functions according to embodiments of the invention.

In this document, the terms "computer program product", "computer-readable medium", and the like, may be used generally to refer to media such as, memory storage devices, or storage unit. These, and other forms of computer-readable media, may be involved in storing one or more instructions for use by processor to cause the processor to perform specified operations. Such instructions, generally referred to as "computer program code" (which may be grouped in the form of computer programs or other groupings), when executed, enable the computing system. In this document, computer readable storage may be a transitory or a non-transitory medium, where non-transitory computer readable storage comprises all computer readable storage with the sole exception of a transitory, propagating signal.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known", and terms of similar meaning, should not be construed as limiting the item described to a given time period, or to an item available as of a given time. But instead these terms should be read to encompass conventional, traditional, normal, or standard technologies that may be available, known now, or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated. The presence of broadening words and phrases such as "one or more," "at least," "but not limited to", or other like phrases in some instances shall not be read to mean that the narrower case is intended or required in instances where such broadening phrases may be absent.

Additionally, memory or other storage, as well as communication components, may be employed in embodiments of the invention. It will be appreciated that, for clarity purposes, the above description has described embodiments of the invention with reference to different functional units and processors. However, it will be apparent that any suitable distribution of functionality between different functional units, processing logic elements or domains may be used without detracting from the invention. For example, functionality illustrated to be performed by separate processing logic elements, or controllers, may be performed by the same processing logic element, or controller. Hence, references to specific functional units are only to be seen as references to suitable means for providing the described functionality, rather than indicative of a strict logical or physical structure or organization.

What is claimed is:

1. An apparatus for automatically identifying a surgical instrument, the apparatus comprising:
   a capture module comprising hardware to capture multiple attributes of the surgical instrument, wherein the capture module comprises an image capture device including at least a first camera and a second camera, wherein the first camera captures a first image of the surgical instrument, wherein the second camera captures a second image of the surgical instrument, and wherein the first and second cameras are relatively positioned to capture respective first and second perspectives of the surgical instrument;
   an attribute database comprising multiple stored attributes of a plurality of reference surgical instruments;
   a comparison module programmed to generate a comparison score for the surgical instrument, wherein the comparison module is programmed to generate the comparison score by receiving multiple attributes captured by the capture module and comparing it to the multiple attributes stored in the attribute database, and wherein the comparison module is programmed to generate the comparison score by at least comparing the first and second images of the surgical instrument to the stored images of the plurality of reference surgical instruments; and
   an exporting module configured to receive and export the comparison score generated by the comparison module,
   wherein the image capture device is configured to capture an image of teeth of the surgical instrument, and wherein the comparison module is programmed to generate the comparison score by at least comparing the captured image of the teeth of the surgical instrument to stored images of teeth of the plurality of reference surgical instruments.

2. The apparatus of claim 1, wherein the capture module further comprises one or more devices selected from the group consisting of: a weight capture device, a color capture device, a material-type capture device, and a surface-type capture device.

3. The apparatus of claim 1, wherein the image capture device further comprises a reference grid for obtaining dimensions of the surgical instrument, wherein the attribute database comprises stored dimensions of the plurality of reference surgical instruments, and wherein the comparison module is programmed to generate the comparison score by at least comparing the dimensions of the surgical instrument to stored dimensions of the plurality of reference surgical instruments.

4. The apparatus of claim 1, wherein the comparison module generates the comparison score by generating a first sub-set of the plurality of reference surgical instruments, wherein the first sub-set comprises one or more of the plurality of reference surgical instruments that exceed a threshold comparison value for one of the at least one stored attribute of the plurality of reference surgical instruments.

5. The apparatus of claim 1, wherein the exporting module comprises a display for displaying the comparison score.

6. A method of identifying a surgical instrument, comprising:
   capturing multiple attributes of the surgical instrument, wherein capturing the multiple attributes comprises capturing at least a first image and a second image of the surgical instrument, wherein the first image and second image provide respective first and second perspectives of the surgical instrument;
   comparing the multiple attributes to multiple attributes of a plurality of reference instruments, wherein the multiple attributes of the plurality of reference instruments is stored in an attribute database, wherein comparing the multiple captured attributes comprises at least comparing the first and second images of the surgical instrument to stored images of the plurality of reference surgical instruments;
   generating a comparison score for the surgical instrument, wherein the comparison score is based on the comparing the multiple captured attributes to the multiple stored attributes of a plurality of reference instruments; and
   exporting the comparison score,
   wherein capturing the multiple attributes comprises capturing an image of teeth of the surgical instrument, and wherein comparing the multiple captured attributes comprises at least comparing the image of the teeth of the surgical instrument to stored images of teeth of the plurality of reference surgical instruments.

7. The method of claim 6, wherein capturing the multiple attributes further comprises capturing one or more attributes selected from the group consisting of: a dimension of the surgical instrument, a weight of the surgical instrument, a color of the surgical instrument, a material-type of the surgical instrument, and a surface-type of the surgical instrument.

8. The method of claim 7, wherein capturing the multiple attributes comprises capturing at least a dimension of the surgical instrument, and wherein comparing the multiple captured attributes comprises comparing at least the dimension of the surgical instrument to stored dimensions of the plurality of reference surgical instruments.

9. The method of claim 6, wherein generating the comparison score comprises generating a first sub-set of the plurality of reference surgical instruments, wherein the first sub-set comprises one or more of the plurality of reference surgical instruments that exceed a threshold comparison value for one of the at least one stored attribute of the plurality of reference surgical instruments.

10. The method of claim 9, wherein generating the comparison score comprises comparing a second of the captured attributes of the surgical instrument to a second of the stored attributes of the plurality of reference surgical instruments.

11. The method of claim 6, wherein exporting the comparison score comprises displaying the comparison score.

12. A method of building a database of at least one attribute of each of a plurality of reference materials, the method comprising:
   determining whether a surgical instrument comprises an identification mark;
   capturing the at least one attribute of the surgical instrument when the surgical instrument is determined not to comprise an identification mark;
   generating an identity of the surgical instrument;
   exporting the at least one attribute and the identity of the surgical instrument to the database;
   capturing multiple attributes of the surgical instrument;
   comparing the multiple attributes to multiple attributes of a plurality of reference instruments, wherein the multiple attributes of the plurality of reference instruments are stored in an attribute database;
   generating a comparison score for the surgical instrument, wherein the comparison score is based on the comparing the multiple captured attribute to multiple attributes of a plurality of reference instruments; and
   exporting the comparison score,
   wherein capturing the multiple attributes comprises capturing an image of teeth of the surgical instrument, and wherein comparing the multiple captured attributes comprises at least comparing the image of the teeth of the surgical instrument to stored images of teeth of the plurality of reference surgical instruments.

13. The method of claim 12, further comprising accessing a manufacturer's database to obtain the at least one attribute.

* * * * *